(12) United States Patent
Elmen et al.

(10) Patent No.: US 9,297,010 B2
(45) Date of Patent: *Mar. 29, 2016

(54) SHORT INTERFERING RNA (SIRNA) ANALOGUES

(71) Applicant: Santaris Pharma A/S, Hoersholm (DK)

(72) Inventors: Joacim Elmen, Stockholm (SE); Claes Wahlestedt, Stockholm (SE); Zicai Liang, Sundbyberg (SE); Anders M. Sorensen, Kobenhavn v (DK); Henrik Orum, Vaerlose (DK); Troels Koch, Copenhagen S (DK)

(73) Assignee: Roche Innovation Center Copenhagen A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/177,458

(22) Filed: Feb. 11, 2014

(65) Prior Publication Data

US 2014/0235844 A1    Aug. 21, 2014

Related U.S. Application Data

(63) Continuation of application No. 10/550,152, filed as application No. PCT/DK2004/000192 on Mar. 22, 2004, now Pat. No. 8,653,252.

(60) Provisional application No. 60/456,888, filed on Mar. 21, 2003.

(30) Foreign Application Priority Data

Mar. 21, 2003 (DK) ................... 2003 00442
Oct. 31, 2003 (DK) ................... 2003 01625
Jan. 30, 2004 (DK) ................... 2004 00145

(51) Int. Cl.
| | |
|---|---|
| C12N 15/113 | (2010.01) |
| A61K 38/09 | (2006.01) |
| A61K 38/20 | (2006.01) |
| A61K 38/21 | (2006.01) |
| A61K 38/31 | (2006.01) |
| C12N 15/11 | (2006.01) |
| A61K 38/00 | (2006.01) |

(52) U.S. Cl.
CPC ............ *C12N 15/1135* (2013.01); *A61K 38/09* (2013.01); *A61K 38/2013* (2013.01); *A61K 38/212* (2013.01); *A61K 38/31* (2013.01); *C12N 15/111* (2013.01); *C12N 15/1131* (2013.01); *A61K 38/00* (2013.01); *C12N 2310/14* (2013.01); *C12N 2310/3231* (2013.01); *C12N 2310/3233* (2013.01); *C12N 2310/3341* (2013.01); *C12N 2310/53* (2013.01); *C12N 2320/51* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 5,898,031 | A | 4/1999 | Crooke |
| 6,107,094 | A | 8/2000 | Crooke |
| 6,506,559 | B1 | 1/2003 | Fire et al. |
| 7,056,704 | B2 | 6/2006 | Tuschl et al. |
| 7,078,196 | B2 | 7/2006 | Tuschl et al. |
| 7,432,250 | B2 | 10/2008 | Crooke |
| 7,589,190 | B2 | 9/2009 | Westergaard et al. |
| 2002/0068709 | A1 | 6/2002 | Orum et al. |
| 2004/0014956 | A1 | 1/2004 | Woolf et al. |
| 2004/0053875 | A1 | 3/2004 | Kreutzer et al. |
| 2004/0180351 | A1 | 9/2004 | Giese et al. |
| 2005/0261212 | A1 | 11/2005 | McSwiggen |
| 2009/0176977 | A1 | 7/2009 | Elmen et al. |
| 2009/0182136 | A1 | 7/2009 | Wengel et al. |

FOREIGN PATENT DOCUMENTS

| | | |
|---|---|---|
| CA | 2459532 | 2/2003 |
| EP | 0928290 | 3/2005 |
| EP | 1214945 | 6/2005 |
| EP | 1407044 | 9/2007 |
| EP | 1550719 | 12/2008 |
| WO | WO99/14226 | 3/1999 |
| WO | WO 0044895 A1 * | 8/2000 |
| WO | WO00/56746 | 9/2000 |
| WO | WO00/56748 | 9/2000 |
| WO | WO00/66604 | 11/2000 |
| WO | WO01/25248 | 4/2001 |
| WO | WO02/28875 | 4/2002 |
| WO | WO02/44321 | 6/2002 |

(Continued)

OTHER PUBLICATIONS

Imanishi et al., "Synthesis and Property of Novel Conformationally Constrained Nucleoside and Oligonucleotide Analogs," The Sixteenth International Congress of Heterocyclic Chemistry 1015:PO1-101 (1997).

(Continued)

*Primary Examiner* — Tracy Vivlemore

(74) *Attorney, Agent, or Firm* — Fish & Richardson P.C.

(57) ABSTRACT

The present invention is directed to novel double-stranded short interfering (siRNA) analogs comprising locked nucleic acid (LNA) monomers. Such compounds induces sequence-specific post-transcriptional gene silencing in many organisms by a process known as RNA interference (RNAi). The compounds disclosed herein has improved properties compared to non-modified siRNAs and may, accordingly, be useful as therapeutic agents, e.g., in the treatment of various cancer forms. More particularly, the present invention is directed to siRNA analogs comprising a sense strand and an antisense strand, wherein each strand comprises 12-35 nucleotides and wherein the siRNA analogs comprise at least one locked nucleic acid (LNA) monomer.

30 Claims, 20 Drawing Sheets

(56) References Cited

FOREIGN PATENT DOCUMENTS

| WO | WO03/006475 | 1/2003 |
| WO | WO03/070918 | 8/2003 |
| WO | WO03/095467 | 11/2003 |
| WO | WO2004/041889 | 5/2004 |
| WO | WO-2004/042046 A2 | 5/2004 |
| WO | WO2004/099387 | 11/2004 |
| WO | WO2005/073378 | 11/2005 |
| WO | WO2006/050734 | 5/2006 |
| WO | WO2007/056153 | 5/2007 |
| WO | WO2007/085485 | 8/2007 |
| WO | WO2007/107162 | 9/2007 |
| WO | WO2008/049078 | 4/2008 |

OTHER PUBLICATIONS

Singh et al., "LNA (locked nucleic acids): synthesis and high-affinity nucleic acid recognition," Chem. Commun, 1998:455-456.

Paushkin et al., "The SMN complex, an assemblyosome of ribonucleoproteins," Curr. Opin. In Cell Biol., 14:305-312 (2002).

Birmingham et al., "3' UTR seed matches, but not overall identity, are associated with RNAi off-targets," Nature Methods (2006), 3(3):199-204.

Bramsen et al., "Improved silencing properties using small internally segmented interfering RNAs," Nucleic Acids Research (2007), 35(17):5886-5897.

Elbashir et al., "Functional anatomy of siRNAs for mediating efficient RNAi in *Drosophila melanogaster* embryo lysate," The EMBO Journal (2001), 20(23):6877-6888.

Elmen et al., "Locked nucleic acid (LNA) mediated improvements in siRNA stability and functionality," Nucleic Acids Research (2005), 33(1):439-447.

Frieden et al., "Expanding the design horizon on antisense oligonucleotides with alpha-L-LNA," Nucleic Acids Research (2003), 31(21):6365-6372.

Jackson et al., "Expression profiling reveals off-target gene regulation by RNAi," Nature Biotechnology (2003), 21(6):635-638.

Jackson et al., "Widespread siRNA "off-target" transcript silencing mediated by seed region sequence complementarity," RNA (2006), 12:1179-1187.

Kumar et al., "The First Analogues of LNA (Locked Nucleic Acids): Phosphorothioate-LNA and 2'-thio-LNA," Bioorganic & Medicinal Chemistry Letters (1998), 8:2219-2222.

Leuschner et al., "Cleavage of the siRNA passenger strand during RISC assembly in human cells," EMBO Reports (2006), 7(3):314-320.

Maiti et al., "QIP, a putative exonuclease, interacts with the Neurospora Argonaute protein and facilitates conversion of duplex siRNA into single strands," Genes & Development (2007), 21:590-600.

Matranga et al., "Passenger-Strand Cleavage Facilitates Assembly of siRNA into Ago2-Containing RNAi Enzyme Complexes," Cell (2005), 123:607-620.

Petersen et al., "LNA: a versatile tool for therapeutics and genomics," Trends in Biotechnology (2003), 21(2):74-81.

Schwarz et al., "Asymmetry in the Assembly of the RNAi Enzyme Complex," Cell (2003), 115:199-208.

Soutschek et al., "Therapeutic silencing of an endogenous gene by systemic administration of modified siRNAs," Nature (2004) 432:173-178.

Fire et al., "Potent and specific genetic inteference by double-stranded RNA in Caenorhabditis elegans", Nature, vol. 391, Feb. 19, 1998, pp. 806-811.

Andrew Fire, "RNA-triggered gene silencing", TIG, vol. 15, No. 9, Sep. 1999, pp. 358-363.

Julia M. Bosher et al., "RNA interference: genetic wand and genetic watchdog", Nature Cell Biology, vol. 2, Feb. 2000, pp. E31-E36.

Anna Wargelius et al., "Double-Stranded RNA Induces Specific Developmental Defects in Zebrafish Embryos", Biochemical and Biophysical Research Communications, vol. 263, (c) 1999, pp. 156-161.

Florence Wianny et al., "Specific interference with gene function by double-stranded RNA in early mouse development", Nature Cell Biology, vol. 2, Feb. 2000, pp. 70-75.

Lena Alexopoulou, "Recognition of double-stranded RNA and activation of NF-kB by Toll-like receptor 3", Nature, Oct. 2001, pp. 732-738.

George Stark et al., "How Cells Respond to Interferons", Annu. Rev. Biochem., vol. 67, (c) 1998, pp. 227-264.

Charles E. Samuel, "Antiviral Actions of Interferons", Clinical Microbiology Reviews, vol. 14, No. 4, Oct. 2001, pp. 778-809.

Phillip D. Zamore et al., RNAi: Double-Stranded RNA Directs the ATP-Dependent Cleavage of mRNA at 21 to 23 Nucleotide Intervals, Cell, vol. 101, (c) 2000, pp. 25-33.

Sayda M. Elbashir et al., "RNA Interference is mediated by 21- and 22-nucleotide RNAs", Genes & Development, vol. 15, (c) 2001, pp. 188-200.

Sayda M. Elbashir et al., "Duplexes f 21-nucleotide RNAs mediate Rna interference in cultured mammalian cells", Nature, vol. 411, May 24, 20061, pp. 494-498.

Michael T. McManus et al., "Gene Silencing in Mammals by Small Interfering RNAs", Nature Reviews Genetics, vol. 3, Oct. 2002, pp. 737-747.

James D. Thompson, "Applications of antisense and siRNAs during preclinical drug development", Drug Discovery Today, vol. 7, No. 17, Sep. 2002, pp. 912-917.

Susan Parrish et al., "Functional Anatomy of a dsRNA Trigger: Differential Requirement for the Two Trigger Strands in RNA Interference", Molecular Cell, vol. 6, Nov. 2000, pp. 1077-1087.

Alexandra Boutla, "Short 5'-phosphorylated double-stranded RNAs induce RNA Interference in *Drosophila*,", Current Biology, vol. 11, (c) 2001, pp. 1776-1780.

Torgeir Holen et al., "Positional effects of short interfering RNAs targeting the human coagulation trigger Tissue Factor", Nucleic Acids Research, vol. 30, No. 8, (c) 2002, pp. 1757-1766.

Hirohiko Hohjoh, "RNA interference (RNAi) induction with various types of synthetic oligonucleotide duplexes in cultured human cells", FEBS Letters 521, FEBS 26179, (c) 2002, pp. 195-199.

M. Hamada et al., Effects on RNA Interference in Gene Expression (RNAi) in Cultured Mammalian Cells of Mismatches and the Introduction of Chemical Modifications at the 3'-Ends of siRNAs, Antisense and Nucleic Acid Drug Development, vol. 12, pp. 301-309, 2002.

Antti Nykanen et al., "ATP Requirements and Small Interfering RNA Structure in the RNA Interference Pathway", Cell, vol. 107, Nov. 2001, pp. 309-321.

Javier Martinez, "Single-Stranded Antisense siRNAs Guide Target RNA Cleavage in RNAi", Cell, vol. 110, pp. 563-574, 2002.

Scott M. Hammond et al., "An RNA-directed nuclease meidates post-transcriptional gene silencing in *Dropsophila* cells", Nature, vol. 404, Mar. 2000, pp. 293-296.

M. Amarzguioui et al., "Tolerance for mutations and chemical modifications in a siRNA", Nucleic Acids Research, vol. 31, No. 2, (c) 2003, pp. 589-595.

D. Braasch et al., "RNA Interference in Mammalian Cells by Chemically-Modified RNA", Biochemistry, vol. 42, (c) 2003, pp. 7967-7975.

Y. Hayakawa et al., "Toward an Ideal Synthesis of Oligonucleotides: Development of a Novel Phosphoramidite Method with High Capability", Bulletin of the chemical society of Japan, vol. 74, No. 9, pp. 1547-1556, 2001.

Dwaine A. Braasch et al., "Novel Antisense and Peptide Nucleic Acid Strategies for Controlling Gene Expression", Biochemistry, vol. 41, No. 14, Apr. 9, 2002, pp. 4503-4510.

\* cited by examiner siRNA/siLNA targeting SARS

| | Start position | | End position |
|---|---|---|---|
| siRNA | | | |
| siRNA SARS 1: | 13,547 | 5'-ggaugaggaaggcaauuautt-3'<br>3'-ttccuacuccuuccguuaaau-5' | 13,567 |
| siRNA SARS 2: | 14,015 | 5'-cugguacgauuucgguugautt-3'<br>3'-ttgaccaugcuaaagccacua-5' | 14,035 |
| siRNA SARS 3: | 14,595 | 5'-acugucaaacccguaauutt-3'<br>3'-ttugacaguuugggccauuaa-5' | 14,615 |
| siRNA SARS 4: | 14,770 | 5'-gacaacuccuauucguagutt-3'<br>3'-ttcuguugaggauaagcauca-5' | 14,790 |
| siLNA | | | |
| siLNA SARS 1: | 13,547 | 5'-GgaugaggaaggcaauuauaTT-3'<br>3'-TTccuacuccuuccguuaaau-5' | 13,567 |
| siLNA SARS 2: | 14,015 | 5'-CugguacgauuucgguugauTT-3'<br>3'-TTgaccaugcuaaagccacua-5' | 14,035 |
| siLNA SARS 3: | 14,595 | 5'-AcugucaaacccguaauuTT-5'<br>3'-TTugacaguuugggccauuaa-5' | 14,615 |
| siLNA SARS 4: | 14,770 | 5'-GacaacuccuauucguaguTT-5'<br>3'-TTcuguugaggauaagcauca-5' | 14,790 |

FIG. 7

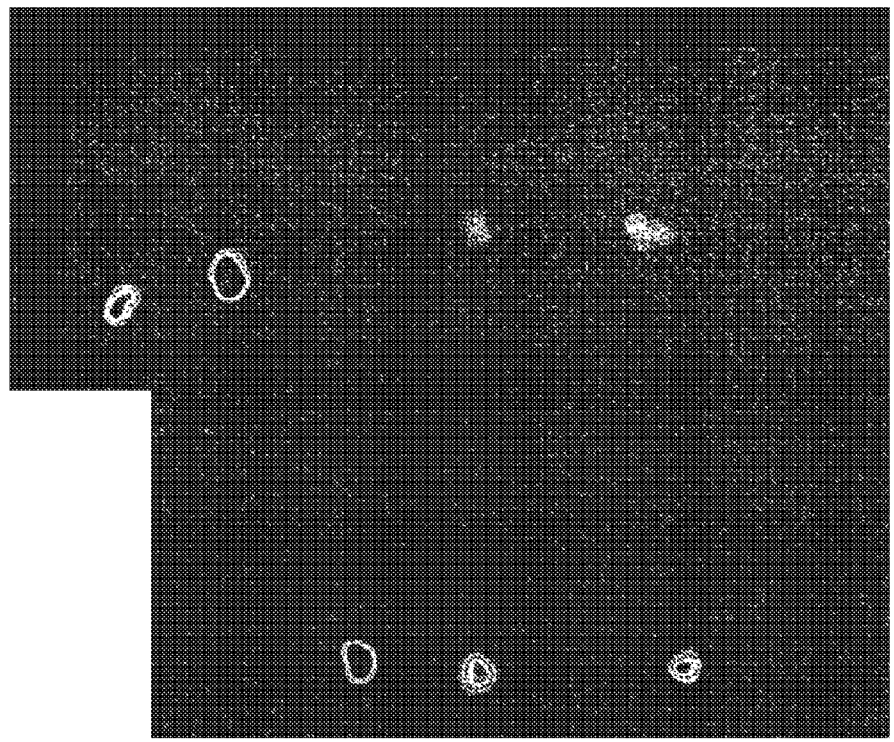
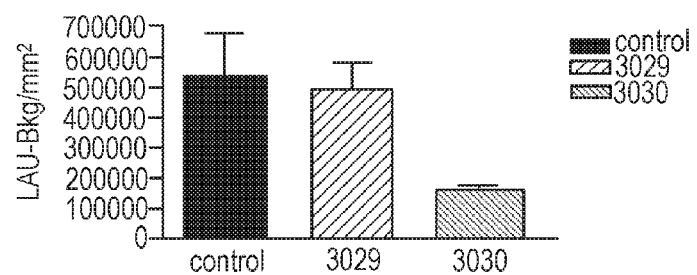
FIG. 18

SHORT INTERFERING RNA (SIRNA) ANALOGUES

RELATED APPLICATIONS

This application is a divisional of U.S. application Ser. No. 10/550,152, filed Jan. 4, 2007, which is a National Stage Entry of PCT/DK04/00192 filed Mar. 22, 2004, which claims priority from Provisional Application 60/456,888 filed Mar. 21, 2003.

SEQUENCE LISTING

The instant application contains a Sequence Listing which has been submitted electronically in ASCII format and is hereby incorporated by reference in its entirety. Said ASCII copy, created on Apr. 14, 2014, is named 22460-0041002_SL.txt and is 34,626 bytes in size.

FIELD OF THE INVENTION

The present invention is directed to novel double-stranded short interfering (siRNA) analogues comprising locked nucleic acid (LNA) monomers. Such compounds induces sequence-specific post-transcriptional gene silencing in many organisms by a process known as RNA interference (RNAi). The compounds disclosed herein has improved properties compared to non-modified siRNAs and may, accordingly, prove useful as therapeutic agents, e.g., in the treatment of various cancer forms.

BACKGROUND OF THE INVENTION

Discovery of RNA interference (RNAi) in *C. Elegans* was made by Fire et al. (Nature, 1998, 391, 806-811). Long stretches of double stranded RNA (dsRNA) was found to have a potent knock-down effect on gene expression that could last for generations in the worm. RNA interference (RNAi) rapidly became a functional genomic tool in *C. Elegans* (early RNA interference is reviewed by Fire (TIG, 1999, 15, 358-363) and Bosher and Labouesse (Nature Cell Biology, 2000, 2, E31-E36)). The first studies where RNA interference was demonstrated to work in vertebrates were performed in zebrafish embryos and mouse oocytes (Wargelius et al., Biochem. Biophys. Res. Corn. 1999, 263, 156-161, Wianny and Zernicka-Goetz, Nature Cell Biology, 2000, 2, 70-75). Since dsRNA induces non-specific effects in mammalian cells it has been argued that these mechanisms were not fully developed in the mouse embryonic system (Alexopoulou et al., Nature, 2001, 413, 732-738, Reviews: Stark et al., Annu. Rev. Biochem., 1998, 67, 227-264 and Samuel, Clin. Micro. Rev., 2001, 14, 778-809).

As far as *C. Elegans* and *Drosophila* are concerned, it has been shown that the long RNAi strands are degraded to short double strands (21-23 nucleotides) and that these degraded forms mediated the interference (Zamore et al., Cell, 2000, 101, 25-33 and Elbashir et al., Gen. Dev., 2001, 15, 188-200). Elbashir et al. (Gen. Dev., 2001, 15, 188-200) showed that a sense or antisense target is cleaved equally and that both strands in siRNA can guide cleavage to target antisense or sense RNA, respectively. It was unambiguously shown by Elbashir et al. (Nature, 2001, 411, 494-498) that the siRNAs mediate potent knock-down in a variety of mammalian cell lines and probably escaped the adverse non-specific effects of long dsRNA in mammalian cells. This discovery was a hallmark in modern biology and the application of siRNAs as therapeutics soon became an attractive field of research (Reviewed by McManus and Sharp, Nature Reviews Genetics, 2002, 3, 737-747 and Thompson, D D T, 2002, 7, 912-917).

DsRNAs are rather stable in biological media. However, the moment the duplex is dissociated into the individual strands these are, by virtue of being RNA, immediately degraded. One of the strategies to bring further stability to siRNA has been to introduce chemically modified RNA residues into the individual strands of the siRNA. It is well known that synthetic RNA analogues are much more stable in biological media, and that the increased stability is also induced to the proximate native RNA residues. By greater stability is mainly meant increased nuclease resistance but also better cellular uptake and tissue distribution may be conferred by such modifications. Several siRNA analogues have been described:

Pre-siRNA (Parrish et al. Mol. Cell, 2000, 6, 1077-1087) show tolerance for certain backbone modifications for RNAi in *C. elegans*. By in vitro transcription of the two different strands in presence of modified nucleotides, it was possible to show that phosphorothioates are tolerated in both the sense and antisense strand and so are 2'-fluorouracil instead of uracil. 2'-Aminouracil and 2'-aminocytidine reduce the RNAi activity when incorporated into the sense strand and the activity is completely abolished when incorporated in the antisense strand. With an exchange of uracil to 2'-deoxythymidine in the sense strand the effect is also reduced, and even more when the exchange is in the antisense strand. If one or both strand(s) consist entirely of DNA monomers, the RNAi activity is abolished. In the above-mentioned study, base modifications were also investigated; It was found that 4-thiouracil and 5-bromouracil are tolerated in both stands, whereas 5-iodouracil and 5-(3-aminoallyl)uracil reduce the effect in the sense strand and even more in the antisense strand. Replacing guanosine with inosine markedly reduces the activity, independently of whether the modification is performed in the sense or antisense strand.

However, UU 3' overhangs can be exchanged with 2' deoxythymidine 3' overhangs and are well tolerated (Elbashir et al., Nature, 2001, 411, 494-498 and Boutla et al., Curr. Biol., 2001, 11, 1776-1780).

It has also been shown that DNA monomers can be incorporated in the sense strand without compromising the activity.

Elbashir et al., EMBO, 2001, 20, 6877-6888) showed that modified siRNA containing four deoxynucleotides in each 3'-end of the siRNA maintained full activity. Furthermore, it was found that the activity was abolished if the siRNA contained only one base-pair mismatch in the "middle" of the molecule.

However, it has also been reported that 1-2 mismatches can be tolerated as long as the mismatches are introduced in the sense strand (Hoien et al, NAR, 2002, 30, 1757-1766; Hohjoh, FEBS Lett., 2002, 26179, 1-5; Hamada et al., Antisense and Nucl. Acid Drug Dev., 2002, 12, 301-309; and Boutla et al., Curr. Biol., 2001, 11, 1776-1780)).

Nykänen et al. (Cell, 2001, 107, 309-321) showed the need for ATP in making siRNA out of RNAi, but also in the later steps to exert the siRNA activity. ATP is needed for unwinding and maintaining a 5'-phosphate for RISC recognition. The 5'-phosphate is necessary for siRNA activity. Martinez et al. (Cell, 2002, 110, 563-574) showed that a single strand can reconstitute the RNA-induced silencing complex (RISC, Hammond et al., Nature, 2000, 404, 293-296) and that a single antisense strand has activity especially when 5'-phosphorylated. 5'-antisense strand modification inhibits activity while both the 3' end and the 5' end of the sense strand can be modified.

Amarzguioui et al. (NAR, 2003, 31, 589-595) confirmed the above-mentioned findings, and it was concluded that a mismatch is tolerated as long as it is not too close to the 5' end of the antisense strand. A mismatch 3-5 nucleotides from the 5' end of the antisense strand markedly diminishes the activity. However, it was shown that two mismatches are tolerated if they are in the "middle" or towards the 3' end of the antisense strand, though with a slightly reduced activity.

Modifications, such as phosphorothioates and 2'-O-methyl RNA, have been introduced at the termini of siRNA (Amarzguioui et al., NAR, 2003, 31, 589-595) and they were well tolerated. 2'-O-allylation reduces the effect when present in the 5' end of the antisense strand The bi-cyclic nucleoside analogue ENA (2'-O,4'-C-ethylene thymidine (ENA thymidine, eT) has also been incorporated into siRNA (Hamada et al., Antisense and Nucl. Acid Drug Dev., 2002, 12, 301-309). It was shown that two ENA thymidines in the 5' end of the sense strand deteriorated the effect. It was concluded by Hamada et al. (2002) that: "using 2'-O,4'-C-ethylene thymidine, which is a component of ethylene-bridged nucleic acids (ENA), completely abolished RNAi".

More recently, a number of siRNAs containing incorporated LNA monomers were described by Braasch et al. (Biochemistry 2003, 42, 7967-7975).

In conclusion, it has been shown that the antisense strand is more sensitive to modifications than is the sense strand. Without being limited to any specific theory, this phenomena is, at least partly, believed to be based on the fact that the structure of the antisense/target duplex has to be native A-form RNA. The sense strand of siRNA can be regarded as a "vehicle" for the delivery of the antisense strand to the target and the sense strand is not participating in the enzyme-catalysed degradation of RNA. Thus, in contrast to the antisense strand, modifications in the sense strand is tolerated within a certain window even though the modifications induce changes to the A-form structure of the siRNA. If changes are introduced in the antisense strand they have to be structurally balanced within the recognition frame of the native RNA induced silencing complex (RISC).

Evidently, there is a need in the field for novel and improved siRNA analogues which possess potent in vivo properties, an increased biostability (corresponding to an increased $T_m$), an increased nuclease resistance, improved cellular uptake and/or improved tissue distribution as compared to the siRNA compounds which are presently available.

Thus, the object of the present invention is to provide improved siRNA analogues having one or more of the above-mentioned improved properties. The present invention thus provides improved siRNA analogues which, inter alfa, show a high degree of biostability and/or nuclease stability and which efficiently targets RNA, such as mRNA or pre-mRNA, or a variety of structural RNAs such as tRNA, snRNA, scRNA, rRNA or even regulatory RNAs like microRNAs

BRIEF DESCRIPTION OF THE INVENTION

Accordingly, in a first aspect the present invention relates to a double-stranded compound comprising a sense strand and an antisense strand, wherein each strand comprises 12-35 nucleotides and wherein said compound comprises at least one locked nucleic acid (LNA) monomer.

In another aspect the present invention relates to a pharmaceutical composition comprising a compound according to the invention and a pharmaceutically acceptable diluent, carrier or adjuvant.

In a further aspect the present invention relates to a compound according to the invention for use as a medicament.

In a still further aspect the present invention relates to the use of a compound according to the invention for the manufacture of a medicament for the treatment of cancer or Severe Acute Respiratory Syndrome (SARS).

In an even further aspect the present invention relates to a method for treating cancer or Severe Acute Respiratory Syndrome (SARS), said method comprising administering a compound according to the invention or a pharmaceutical composition according to the invention to a patient in need thereof.

Other aspects of the present invention will be apparent from the below description and the appended claims.

BRIEF DESCRIPTION OF THE DRAWINGS

FIG. 7 shows siLNA and siRNA compounds for targeting SARS. Capital letters: Beta-D-oxy LNA monomer. Small letters: RNA monomer.

FIG. 18 shows the in vivo anti-tumour effect of two anti-EGFP siLNAs (3029/3031 and 3030/3031) on 15PC3-EGFP xenograft NMRI mice.

DETAILED DESCRIPTION OF THE INVENTION

Definitions

Figure 1:
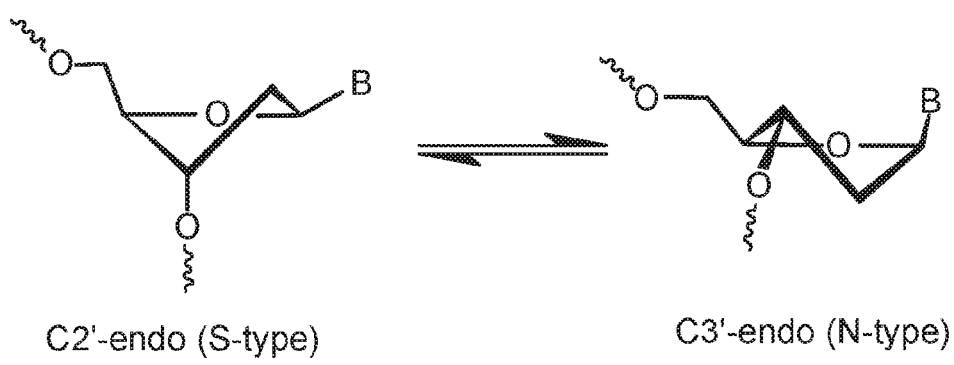
FIG. 1 shows the two furanose conformations (S-type and N-type).

In the present context the term "nucleotide" means a 2-deoxyribose (DNA) unit or a ribose (RNA) unit which is bonded through its number one carbon to a nitrogenous base, such as adenine (A), cytosine (C), thymine (T), guanine (G) or uracil (U), and which is bonded through its number five carbon atom to an internucleoside linkage group (as defined below) or to a terminal groups (as defined below). Accordingly, when used herein the term "nucleotide" encompasses RNA units (or monomers) comprising a ribose unit which is bonded through its number one carbon to a nitrogenous base, such as A, C, T, G or U, and which is bonded through its number five carbon atom to a phosphate group or to a terminal group. Analogously, the term "nucleotide" also encompasses DNA units (or monomers) comprising a 2-deoxyribose unit which is bonded through its number one carbon to a nitrogenous base, such as A, C, T, G or U, and which is bonded through its number five carbon atom to a phosphate group or to a terminal group. The term "nucleotide" also covers variants or analogues of such RNA and DNA monomers. A detailed disclosure of such RNA and DNA monomer variants or analogues are given below.

In the present context the term "nucleoside" means a 2-deoxyribose (DNA) unit or a ribose (RNA) unit which is bonded through its number one carbon to a nitrogenous base, such as adenine (A), cytosine (C), thymine (T), guanine (G) or uracil (U). Accordingly, when used herein the term "nucleoside" encompasses RNA units (or monomers) comprising a ribose unit which is bonded through its number one carbon to a nitrogenous base, such as A, C, T, G or U. Analogously, the term "nucleoside" also encompasses DNA units (or monomers) comprising a 2-deoxyribose unit which is bonded through its number one carbon to a nitrogenous base, such as A, C, T, G or U. The term "nucleoside" also covers variants or analogues of such RNA and DNA monomers. It will be understood that the individual nucleosides are linked together by an internucleoside linkage group.

When used in the present context, the terms "locked nucleic acid monomer", "locked nucleic acid residue", "LNA monomer" or "LNA residue" refer to a bicyclic nucleotide analogue. LNA monomers are described in inter alia WO 99/14226, WO 00/56746, WO 00/56748, WO 01/25248, WO 02/28875, WO 03/006475 and WO 03/095467. The LNA monomer may also be defined with respect to its chemical formula. Thus, a "LNA monomer" as used herein has the chemical structure shown in Scheme 2 below:

Scheme 2

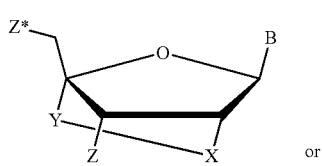

or

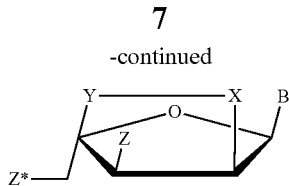

wherein
- X is selected from the group consisting of O, S and $NR^H$, where $R^H$ is H or alkyl, such as $C_{1-4}$-alkyl;
- Y is $(-CH_2)_r$, where r is an integer of 1-4; with the proviso that when X=O then r is not 2.
- Z and Z* are independently absent or selected from the group consisting of an internucleoside linkage group, a terminal group and a protection group; and
- B is a nucleobase. A detailed disclosure of preferred LNA monomers are given below.

The term "internucleoside linkage group" is intended to mean a group capable of covalently coupling together two nucleosides, two LNA monomers, a nucleoside and a LNA monomer, etc. Specific and preferred examples include phosphate groups and phosphorothioate groups.

The term "nucleic acid" is defined as a molecule formed by covalent linkage of two or more nucleotides. The terms "nucleic acid" and "polynucleotide" are used interchangeable herein. When used herein, a "nucleic acid" or a "polynucleotide" typically contains more than 35 nucleotides.

The term "oligonucleotide" refers, in the context of the present invention, to an oligomer (also called oligo) of RNA, DNA and/or LNA monomers as well as variants and analogues thereof. When used herein, an "oligonucleotide" typically contains 2-35 nucleotides, in particular 12-35 nucleotides.

By the term "improved properties" is understood one or more property by which the siLNA compound of the invention show better overall performance as compared to its native counterparts. Examples of such parameters are ease of production, cost of production, longer shelf life, higher binding affinity to target (interim complement in siLNA or mRNA target), higher ability to penetrate a cell membrane, better resistance to extra- and intracellular nucleases, easier to formulate pharmaceutically, higher potency in mode of action, better tissue distribution, better phenotypic response, longer lasting effects, etc.

By the terms "unit" or "residue" is understood a monomer.

The term "at least one" encompasses an integer larger than or equal to 1, such as 1, 2, 3, 4, 5, 6, 7, 8, 9, 10, 11, 12, 13, 14, 15, 16, 17 and so forth.

The terms "a" and "an" as used about a nucleotide, a nucleoside, an active agent, a LNA monomer, etc. is intended to mean one or more. In particular, the expression "a component (such as a nucleotide, a nucleoside, an active agent, a LNA monomer or the like) selected from the group consisting of." is intended to mean that one or more of the cited components may be selected. Thus, expressions like "a component selected from the group consisting of A, B and C" is intended to include all combinations of A, B and C, i.e. A, B, C, A+B, A+C, B+C and A+B+C.

The term "thio-LNA" refers to a locked nucleotide in which X in Scheme 2 is S. Thio-LNA can be in both the beta-D form and in the alpha-L form. Generally, the beta-D form of thio-LNA is preferred. The beta-D form of thio-LNA is shown in Scheme 3 as compound 3C.

The term "amino-LNA" refers to a locked nucleotide in which X in Scheme 2 is NH or $NR^H$, where $R^H$ is hydrogen or $C_{1-4}$-alkyl. Amino-LNA can be in both the beta-D and alpha-L form. Generally, the beta-D form of amino-LNA is preferred. The beta-D form of amino-LNA is shown in Scheme 3 as compound 3D.

The term "oxy-LNA" refers to a locked nucleotide in which X in Scheme 2 is O. oxy-LNA can be in both the beta-D form and alpha-L form. The beta-D form of oxy-LNA is preferred. The beta-D form and the alpha-L form are shown in Scheme 3 as compounds 3A and 3B, respectively.

The term "siLNA" is broadly used about the double-stranded compounds of the invention. Thus, a "siLNA", as used herein, always comprises at least one LNA monomer.

As used herein, the term "siRNA" refers to a double stranded stretch of RNA or modified RNA monomers. In a typical siRNA compound, the two strands usually have 19 nucleotides complementary to each other thereby creating a double strand that is 19 nucleotides long and each strand having a 3'-end of two overhanging nucleotides. This is not a strict definition of siRNA, which may be slightly longer or shorter, and with or without overhangs. In siRNA one strand is guiding and complementary to the target RNA (antisense strand), and the other strand (sense strand) has the same sequence as the target RNA and hence is complementary to the guiding/antisense strand. Herein, regulatory RNAs such as "micro RNA" ("miRNA") and "short RNA" ("shRNA") and a variety of structural RNAs such as tRNA, snRNA, scRNA, rRNA are used interchangeably with the term "siRNA".

As used herein, the term "mRNA" means the presently known mRNA transcript(s) of a targeted gene, and any further transcripts, which may be identified.

As used herein, the term "target nucleic acid" encompass any RNA that would be subject to modulation, targeted cleavage, steric blockage (decrease the abundance of the target RNA and/or inhibit translation) guided by the antisense strand. The target RNA could, for example, be genomic RNA, genomic viral RNA, mRNA or a pre-mRNA As used herein, the term "target-specific nucleic acid modification" means any modification to a target nucleic acid.

As used herein, the term "gene" means the gene including exons, introns, non-coding 5' and 3' regions and regulatory elements and all currently known variants thereof and any further variants, which may be elucidated.

As used herein, the term "modulation" means either an increase (stimulation) or a decrease (inhibition) in the expression of a gene. In the present invention, inhibition is the preferred form of modulation of gene expression and mRNA is a preferred target.

As used herein, the term "targeting" an siLNA or siRNA compound to a particular target nucleic acid means providing the siRNA or siLNA oligonucleotide to the cell, animal or human in such a way that the siLNA or siRNA compounds are able to bind to and modulate the function of the target.

As used herein, "hybridisation" means hydrogen bonding, which may be Watson-Crick, Hoogsteen, reversed Hoogsteen hydrogen bonding, etc., between complementary nucleoside or nucleotide bases. The four nucleobases commonly found in DNA are G, A, T and C of which G pairs with C, and A pairs with T. In RNA T is replaced with uracil (U), which then pairs with A. The chemical groups in the nucleobases that participate in standard duplex formation constitute the Watson-Crick face. Hoogsteen showed a couple of years later that the purine nucleobases (G and A) in addition to their Watson-Crick face have a Hoogsteen face that can be recognised from the outside of a duplex, and used to bind pyrimidine oligonucleotides via hydrogen bonding, thereby forming a triple helix structure.

In the context of the present invention "complementary" refers to the capacity for precise pairing between two nucleotides sequences with one another. For example, if a nucleotide at a certain position of an oligonucleotide is capable of hydrogen bonding with a nucleotide at the corresponding position of a DNA or RNA molecule, then the oligonucleotide and the DNA or RNA are considered to be complementary to each other at that position. The DNA or RNA strand are considered complementary to each other when a sufficient number of nucleotides in the oligonucleotide can form hydrogen bonds with corresponding nucleotides in the target DNA or RNA to enable the formation of a stable complex. To be stable in vitro or in vivo the sequence of a siLNA or siRNA compound need not be 100% complementary to its target nucleic acid. The terms "complementary" and "specifically hybridisable" thus imply that the siLNA or siRNA compound binds sufficiently strong and specific to the target molecule to provide the desired interference with the normal function of the target whilst leaving the function of non-target mRNAs unaffected In the present context the term "conjugate" is intended to indicate a heterogenous molecule formed by the covalent attachment of a compound as described herein to one or more non-nucleotide or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethelene glycol.

In the present context, the term "$C_{1-6}$-alkyl" is intended to mean a linear or branched saturated hydrocarbon chain wherein the longest chains has from one to six carbon atoms, such as methyl, ethyl, n-propyl, isopropyl, n-butyl, isobutyl, sec-butyl, tert-butyl, pentyl, isopentyl, neopentyl and hexyl. A branched hydrocarbon chain is intended to mean a $C_{1-6}$-alkyl substituted at any carbon with a hydrocarbon chain.

In the present context, the term "$C_{1-4}$-alkyl" is intended to mean a linear or branched saturated hydrocarbon chain wherein the longest chains has from one to four carbon atoms, such as methyl, ethyl, n-propyl, isopropyl, n-butyl, isobutyl, sec-butyl and tert-butyl. A branched hydrocarbon chain is intended to mean a $C_{1-4}$-alkyl substituted at any carbon with a hydrocarbon chain.

When used herein the term "$C_{3-6}$-alkoxy" is intended to mean $C_{1-6}$-alkyl-oxy, such as methoxy, ethoxy, n-propoxy, isopropoxy, n-butoxy, isobutoxy, sec-butoxy, tert-butoxy, pentoxy, isopentoxy, neopentoxy and hexoxy.

In the present context, the term "$C_{2-6}$-alkenyl" is intended to mean a linear or branched hydrocarbon group having from two to six carbon atoms and containing one or more double bonds. Illustrative examples of $C_{2-6}$-alkenyl groups include allyl, homo-allyl, vinyl, crotyl, butenyl, butadienyl, pentenyl, pentadienyl, hexenyl and hexadienyl. The position of the unsaturation (the double bond) may be at any position along the carbon chain.

In the present context the term "$C_{2-6}$-alkynyl" is intended to mean linear or branched hydrocarbon groups containing from two to six carbon atoms and containing one or more triple bonds. Illustrative examples of $C_{2-6}$-alkynyl groups include acetylene, propynyl, butynyl, pentynyl and hexynyl. The position of unsaturation (the triple bond) may be at any position along the carbon chain. More than one bond may be unsaturated such that the "$C_{2-6}$-alkynyl" is a di-yne or enediyne as is known to the person skilled in the art.

The term "carcinoma" is intended to indicate a malignant tumor of epithelial origin. Epithelial tissue covers or lines the body surfaces inside and outside the body. Examples of epithelial tissue are the skin and the mucosa and serosa that line the body cavities and internal organs, such as intestines, urinary bladder, uterus, etc. Epithelial tissue may also extend into deeper tissue layers to from glands, such as mucus-secreting glands.

The term "sarcoma" is intended to indicate a malignant tumor growing from connective tissue, such as cartilage, fat, muscles, tendons and bones.

The term "glioma", when used herein, is intended to cover a malignant tumor originating from glial cells.

Compounds of the Invention

The present invention is, in part, based on the surprising finding that LNA can be used to improve RNA interference by incorporating LNA monomers in the sense and/or antisense strand of double-stranded polynucleotides, such as siRNA. This is particularly surprising as the structurally closely related ENA monomers strongly deteriorates RNA interference, even for minimally modified siRNAs (Hamada et al., Antisense and Nucl. Acid Drug Dev., 2002, 12, 301-309).

LNA exhibits unprecedented binding properties towards DNA and RNA target sequences. In addition to these remarkable hybridization properties, LNA monomers can be mixed and act cooperatively with DNA and RNA monomers as well as with nucleotide analogues, such as 2'-O-alkyl-modified RNA monomers. The unprecedented binding affinity of LNA towards DNA or RNA target sequences, and the ability to mix LNA monomers freely with DNA and RNA monomers and a range of nucleotide analogues has some important consequences for the development of effective and safe siRNA-like compounds.

Natural dsDNA exists at physiological pH as a B-form helix, whereas dsRNA exists as an A-form helix. This morphological difference is due to the difference in the preferred sugar conformations of the deoxyriboses and the riboses. At room temperature the furanose ring of deoxyribose exists in an equilibrium between C2'-endo (S-type) and C3'-endo (N-type) conformation with an energy barrier of ~2 kcal/mol (FIG. 1). The C2'-endo (S-type) conformation gives rise to the B-form helix, whereas the C3'-endo (N-type) conformation gives rise to the A-form helix. For deoxyribose the S-type conformation is slightly lowered in energy compared to the N-type and that explains why DNA is found in the S-type conformation. For ribose the N-type conformation is preferred and, therefore, RNA adopts the A-form helix. It is known that the A-form helix is associated with higher hybridisation stability.

LNA monomers are locking the conformation of the furanose ring in a conformation that corresponds to an extreme C3'-endo conformation. These monomers are therefore mimicking the RNA conformation, and it has been shown that the structure of the oligonucleotide and duplexes of the monomers are RNA-like (Petersen et al., J. Am. Chem. Soc., 2002, 124, 5974-82). This means that the structure of RNA oligonucleotides and RNA/RNA duplexes in which LNA monomers are incorporated are not significantly changed compared to native RNA oligonucleotides and RNA/RNA duplexes. It was furthermore shown that the LNA monomers induced RNA-like conformation when introduced in DNA. Thus, the LNA monomers imposed, in particular at the 3' end, a strong degree of C3'-endo conformation (RNA like). If, for instance, every second or third residue in a DNA oligomer is replaced with LNA monomers, the overall structure of the oligonucleotide will become much like RNA. Thus, the duplex formed by such oligonucleotides will attain a structure resembling native A-form duplexes (RNA/RNA). It is part of this invention to use this property of the LNA monomers to direct the conformation of DNA towards RNA structure.

It will be appreciated that the unprecedented affinity of the LNA may be used to shorten the usual length of a siRNA oligonucleotide (from 21-35 mers to, e.g., 12-20 mers) without compromising the affinity required for pharmacological activity. As the intrinsic specificity of an oligonucleotide is inversely correlated to its length, such a shortening will significantly increase the specificity of the siLNA compound towards its RNA target. One aim of the invention is therefore, due to the fact that the sequence of the humane genome is available and the annotation of its genes is rapidly progressing, to identify the shortest possible, unique sequences in the target mRNA. Moreover, by reducing the size of the oligonucleotides, and thereby ease the manufacturing process and lowering the manufacturing costs, it is believed that siLNA compounds, such as those disclosed herein, have the potential to become the basis for RNAi therapy, and to become a commercially competitive treatment which may be offered for a variety of diseases.

Accordingly, in its broadest aspect the present invention relates to a double-stranded compound comprising a sense strand and an antisense strand, wherein each strand comprises 12-35 nucleotides and wherein said compound comprises at least one locked nucleic acid (LNA) monomer. The double-stranded compounds of the invention may be composed entirely of LNA monomers or it may be composed of LNA monomers in any combination with DNA monomer, RNA monomers or nucleotide analogues.

As indicated above, the term "nucleotide" means a 2-deoxyribose (DNA) unit or a ribose (RNA) unit which is bonded through its number one carbon to a nitrogenous base, such as adenine (A), cytosine (C), thymine (T), guanine (G) or uracil (U), and which is bonded through its number five carbon atom to an internucleoside linkage group (as defined above) or to a terminal group (as discussed below). Thus, the term "nucleotide" encompasses RNA units (or monomers) comprising a ribose unit which is bonded through its number one carbon to a nitrogenous base, such as A, C, T, G or U, and which is bonded through its number five carbon atom to a phosphate group or to a terminal group. As explained above, the term "nucleotide" also encompasses DNA units (or monomers) comprising a 2-deoxyribose unit which is bonded through its number one carbon to a nitrogenous base, such as A, C, T, G or U, and which is bonded through its number five carbon atom to a phosphate group or to a terminal group. The term "nucleotide" also covers variants or analogues of such RNA and DNA monomers. For example, the 2'-OH (RNA) or 2'-H (DNA) group may be substituted with —O—$CH_3$, —O—$CH_2$—$CH_2$—$OCH_3$, —O—$CH_2$—$CH_2$—$CH_2$—$NH_2$, —O—$CH_2$—$CH_2$—$CH_2$—OH or F. Other examples of a nucleotide analogues are LNA monomers. Also, the internucleoside linkage group is not limited to phosphate (—O—P(O)$_2$—O—), but may include —O—P(O,S)—O—, —O—P(S)$_2$—O—, —S—P(O)$_2$—O—, —S—P(O,S)—O—, —S—P(S)$_2$—O—, —O—PO($R^H$)—O—, O—PO($OCH_3$)—O—, —O—PO($NR^H$)—O—, —O—PO($OCH_2CH_2S$—R)—O—, —O—PO($BH_3$)—O—, —O—PO($NHR^H$)—O—, —O—P(O)$_2$—$NR^H$—, —$NR^H$—P(O)$_2$—O—, —$NR^H$—CO—O—, —$NR^H$—CO—$NR^H$—, —O—CO—O—, —O—CO—$NR^H$—, —$NR^H$—CO—$CH_2$—, —O—$CH_2$—CO—$NR^H$—, —O—$CH_2$—$CH_2$—$NR^H$—, —CO—$NR^H$—$CH_2$—, —$CH_2$—$NR^H$—CO—, —O—$CH_2$—$CH_2$—S—, —S—$CH_2$—$CH_2$—O—, —S—$CH_2$—$CH_2$—S—, —$CH_2$—$SO_2$—$CH_2$—, —$CH_2$—CO—$NR^H$—, —O—$CH_2$—$CH_2$—$NR^H$—CO—, —$CH_2$—$NCH_3$—O—$CH_2$—, where $R^H$ is hydrogen or $C_{1-4}$-alkyl.

Furthermore, the nitrogenous base is not restricted to A, C, T, G or U, but may include other purines and pyrimidines, such as 5-methylcytosine, isocytosine, pseudoisocytosine, 5-bromouracil, 5-propynyluracil, 5-propyny-6-fluoroluracil, 5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine. Other examples of nucleotide variants and analogues which fall within the present definition of "nucleotide" are described in Freier & Altmann (Nucl. Acid Res., 1997, 25, 4429-4443) and Uhlmann (Curr. Opinion in Drug & Development (2000, 3(2): 293-213). Scheme 1 below illustrates selected examples of such nucleotide variants and analogous. In conclusion, the compounds of the invention may contain any of the above-mentioned nucleotides as long as the compound contains at least one LNA monomer in at least one of the strands.

Scheme 1

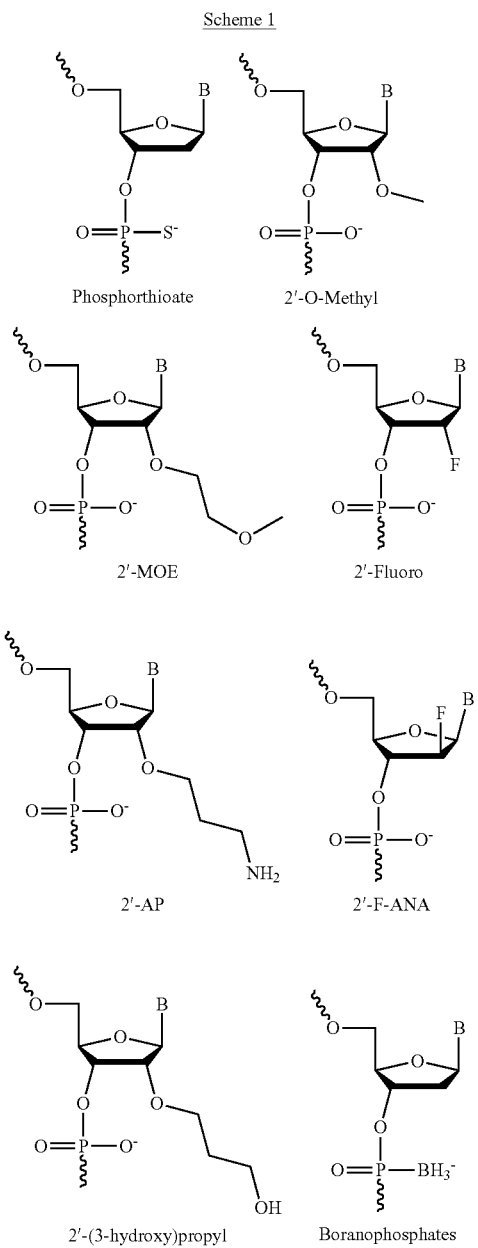

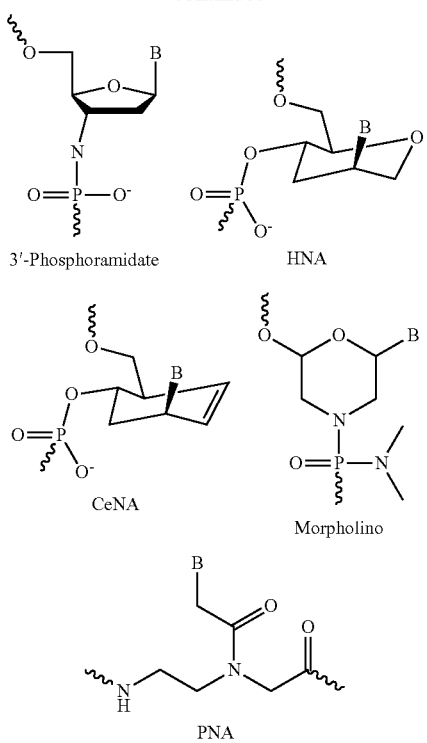

3'-Phosphoramidate HNA

CeNA Morpholino

PNA

As indicated above, the term "locked nucleic acid monomer" or "LNA monomer" refers to a bicyclic nucleotide analogue and has the chemical structure shown in Scheme 2 below:

Scheme 2

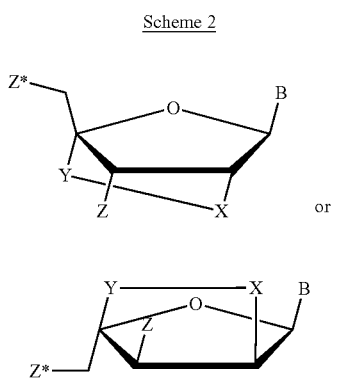

2A or

2B wherein

X is selected from the group consisting of O, S and $NR^H$, where $R^H$ is H or alkyl, such as $C_{1-4}$-alkyl;

Y is $(-CH_2)_r$, where r is an integer of 1-4; with the proviso that when X=O then r is not 2.

Z and Z* are independently absent or selected from the group consisting of an internucleoside linkage group, a terminal group and a protection group; and B is a nucleobase.

In a preferred embodiment of the invention, r is 1, i.e. a preferred LNA monomer has the chemical structure shown in Scheme 3 below:

Scheme 3

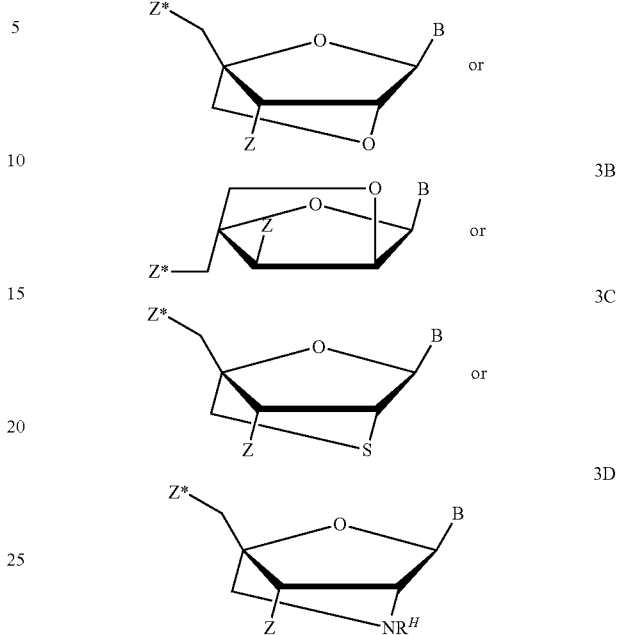

3A or

3B or

3C or

3D wherein Z, Z*, $R^H$ and B are defined above.

In an even more preferred embodiment of the invention, X is O and r is 1, i.e. an even more preferred LNA monomer has the chemical structure shown in Scheme 4 below:

Scheme 4

3A or

3B wherein Z, Z* and B are defined above.

The structures shown in 3A and 3B above may also be referred to as the "beta-D form" and the "alpha-L form", respectively. In a highly preferred embodiment of the invention, the LNA monomer is the beta-D form, i.e. the LNA monomer has the chemical structure indicated in 3A above.

As indicated above, Z and Z*, which serve for an internucleoside linkage, are independently absent or selected from the group consisting of an internucleoside linkage group, a terminal group and a protection group depending on the actual position of the LNA monomer within the compound. It will be understood that in embodiments where the LNA monomer is located at the 3' end, Z is a terminal group and Z* is an internucleoside linkage. In embodiments where the LNA monomer is located at the 5' end, Z is absent and Z* is a terminal group. In embodiments where the LNA monomer is located within the nucleotide sequence, Z is absent and Z* is an internucleoside linkage group.

Specific examples of internucleoside linkage groups include —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, —O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$—CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—CH$_2$—NCH$_3$—O—CH$_2$—, where R$^H$ is hydrogen or C$_{1-4}$-alkyl.

In a preferred embodiment of the invention, the internucleoside linkage group is a phosphate group (—O—P(O)$_2$—O—), a phosphorothioate group (—O—P(O,S)—O—) or the compound may contain both phosphate groups and phosphorothioate groups.

Specific examples of terminal groups include terminal groups selected from the group consisting of hydrogen, azido, halogen, cyano, nitro, hydroxy, Prot-O—, Act-O—, mercapto, Prot-S—, Act-S—, C$_{1-6}$-alkylthio, amino, Prot-N(R$^H$)—, Act-N(R$^H$)—, mono- or di(C$_{1-6}$-alkyl)amino, optionally substituted C$_{1-6}$-alkoxy, optionally substituted C$_{1-6}$-alkyl, optionally substituted C$_{2-6}$-alkenyl, optionally substituted C$_{2-5}$-alkenyloxy, optionally substituted C$_{2-6}$-alkynyl, optionally substituted C$_{2-6}$-alkynyloxy, monophosphate including protected monophosphate, monothiophosphate including protected monothiophosphate, diphosphate including protected diphosphate, dithiophosphate including protected dithiophosphate, triphosphate including protected triphosphate, trithiophosphate including protected trithiophosphate, where Prot is a protection group for —OH, —SH and —NH(R$^H$), and Act is an activation group for —OH, —SH, and —NH(R$^H$), and R$^H$ is hydrogen or C$_{1-5}$-alkyl.

Examples of phosphate protection groups include S-acetylthioethyl (SATE) and S-pivaloylthioethyl (t-butyl-SATE).

Still further examples of terminal groups include DNA intercalators, photochemically active groups, thermochemically active groups, chelating groups, reporter groups, ligands, carboxy, sulphono, hydroxymethyl, Prot-O—CH$_2$—, Act-O—CH$_2$—, aminomethyl, Prot-N(R$^H$)—CH$_2$—, Act-N(R$^H$)—CH$_2$—, carboxymethyl, sulphonomethyl, where Prot is a protection group for —OH, —SH and —NH(R$^H$), and Act is an activation group for —OH, —SH, and —NH(R$^H$), and R$^H$ is hydrogen or C$_{1-6}$-alkyl.

Examples of protection groups for —OH and —SH groups include substituted trityl, such as 4,4'-dimethoxytrityloxy (DMT), 4-monomethoxytrityloxy (MMT); trityloxy, optionally substituted 9-(9-phenyl)xanthenyloxy (pixyl), optionally substituted methoxytetrahydropyranyloxy (mthp); silyloxy, such as trimethylsilyloxy (TMS), triisopropylsilyloxy (TIPS), tert-butyldimethylsilyloxy (TBDMS), triethylsilyloxy, phenyldimethylsilyloxy; tert-butylethers; acetals (including two hydroxy groups); acyloxy, such as acetyl or halogen-substituted acetyls, e.g. chloroacetyloxy or fluoroacetyloxy, isobutyryloxy, pivaloyloxy, benzoyloxy and substituted benzoyls, methoxymethyloxy (MOM), benzyl ethers or substituted benzyl ethers such as 2,6-dichlorobenzyloxy (2,6-C$_{12}$Bzl). Moreover, when Z or Z* is hydroxyl they may be protected by attachment to a solid support, optionally through a linker.

Examples of amine protection groups include fluorenylmethoxycarbonylamino (Fmoc), tert-butyloxycarbonylamino (BOC), trifluoroacetylamino, allyloxycarbonylamino (alloc, AOC), Z-benzyloxycarbonylamino (Cbz), substituted benzyloxycarbonylamino, such as 2-chloro benzyloxycarbonylamino (2-CIZ), monomethoxytritylamino (MMT), dimethoxytritylamino (DMT), phthaloylamino, and 9-(9-phenyl)xanthenylamino (pixyl).

The activation group preferably mediates couplings to other residues and/or nucleotide monomers and after the coupling has been completed the activation group is typically converted to an internucleoside linkage. Examples of such activation groups include optionally substituted O-phosphoramidite, optionally substituted O-phosphortriester, optionally substituted O-phosphordiester, optionally substituted H-phosphonate, and optionally substituted O-phosphonate. In the present context, the term "phosphoramidite" means a group of the formula —P(OR$^x$)—N(R$^y$)$_2$, wherein R$^x$ designates an optionally substituted alkyl group, e.g. methyl, 2-cyanoethyl, or benzyl, and each of R$^y$ designates optionally substituted alkyl groups, e.g. ethyl or isopropyl, or the group —N(R$^y$)$_2$ forms a morpholino group (—N(CH$_2$CH$_2$)$_2$O). R$^x$ preferably designates 2-cyanoethyl and the two R$^y$ are preferably identical and designates isopropyl. Accordingly, a particularly preferred phosphoramidite is N,N-diisopropyl-O-(2-cyanoethyl)phosphoramidite.

As indicated above, B is a nucleobase which may be of natural or non-natural origin. Specific examples of nucleobases include adenine (A), cytosine (C), 5-methylcytosine ($^{Me}$C), isocytosine, pseudoisocytosine, guanine (G), thymine (T), uracil (U), 5-bromouracil, 5-propynyluracil, 5-propyny-6-fluorouracil, 5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine. Preferred nucleobases include A, C, $^{Me}$C, G, T and U, in particular A, C, $^{Me}$C, G and U.

In one embodiment of the invention, the sense strand comprises at least one LNA monomer, such as 1-10 LNA monomers, e.g. 1-5 LNA monomers. In another embodiment of the invention, the antisense strand comprises at least one LNA monomer, such as 1-10 LNA monomers, e.g. 1-5 LNA monomers. In a further embodiment of the invention, the sense strand comprises at least one LNA monomer and the antisense strand comprises at least one LNA monomer. For example, the sense strand typically comprises 1-10 LNA monomers, such as 1-5 LNA monomers, and the antisense strand typically comprises 1-10 LNA monomers, such as 1-5 LNA monomers.

One particular advantage about the compounds of the invention is their improved stability in biological fluids, such as serum. Thus, one embodiment of the invention includes the incorporation of LNA monomers into a standard DNA or RNA oligonucleotide to increase the stability of the resulting siLNA compound in biological fluids e.g. through the increase of resistance towards nucleases (endonucleases and exonucleases). Accordingly, the compounds of the invention will, due to incorporation of LNA monomers, exhibit an increased circulation half-life as a result of its increased melting temperature and/or its increased nuclease resistance. The extent of stability will depend on the number of LNA monomers used, their position in the oligonucleotides and the type of LNA monomer used. Compared to DNA and phosphorothioates the following order of ability to stabilise an oligonucleotide against nucleolytic degradation can be established: DNA<<phosphorothioates, LNA-phosphordiester<LNA-phosphorothioates.

Therefore, compounds according to the invention which are particularly preferred are such compounds which, when incubated in serum (e.g. human, bovine or mice serum), such as in 10% foetal bovine serum in a physiological salt solution at 37° C. for 5 hours, are degraded to a lesser extent than the corresponding dsRNA compound. Preferably, less than 25% of the initial amount of the compound of the invention is degraded after 5 hours, more preferably less than 50% of the initial amount of the compound of the invention is degraded after 5 hours, even more preferably less than 75% of the initial amount of the compound of the invention is degraded after 5 hours. In another embodiment, it is preferred that less than 25% of the initial amount of the compound of the invention is degraded after 10 hours, and even more preferred that less than 50% of the initial amount of the compound of the invention is degraded after 10 hours.

Given the fact that INA synthesis is compatible with standard RNA/DNA synthesis and that the LNA monomers mix freely with many contemporary nucleic acid analogues, nuclease resistance of siLNA compounds can be further enhanced according to the invention by either incorporating other analogues that display increased nuclease stability or by exploiting nuclease-resistant internucleoside linkages e.g. phosphoromonothioate, phosphorodithioate, and methylphosphonate linkages, etc.

LNA monomers can be used freely in the design of siLNA at both 3' overhangs and the 5° end of the sense strand with full activation of the siLNA effect and down-regulation of protein production (>90% reduction). LNA monomers can be distributed quite freely over the sense strand in the siLNA with maintaining high down-regulating capability (80% reduction). The 5' end of the antisense strand in the siLNA can also be modified by LNA monomers, thereby giving rise to down-regulatory capabilities of up to 50-70%. Using a highly LNA monomer-substituted antisense strand does not seem to give a down-regulatory effect, although it can not be ruled out that special design of that combination can elicit a RNAi effect. LNA monomer substitutions of the 3' overhangs along with the 5' end of the sense strand of the siLNA give the highest reduction of protein levels. The 5' end of the antisense strand is the most sensitive to the LNA monomer modification while many other sites of modification are better tolerated.

In one embodiment the siLNA compound is designed so that the LNA monomers are incorporated in the compound in such a way that they are strengthening the basepairs in the duplex at the 5' end of the sense strand. The helicase can there by be directed to unwinde from the other 5' end (antisense strand 5' end). In this way the incorporation of the antisense/guiding strand into RISC can be controlled. The helicase starts unwinding the siRNA duplex at the weakest binding end. The released 3' end is probably targeted for degradation while the remaining strand is incorporated in the RISC. Efficient siRNAs show accumulation of the antisense/guiding strand and weaker base pairing in the 5' end of the antisense/guiding strand. Unwanted side effects may possibly be avoided by having only the correct strand (the antisense/guiding strand) in RISC and not the unwanted sense strand (not complementary to the desired target RNA).

Figure 11:
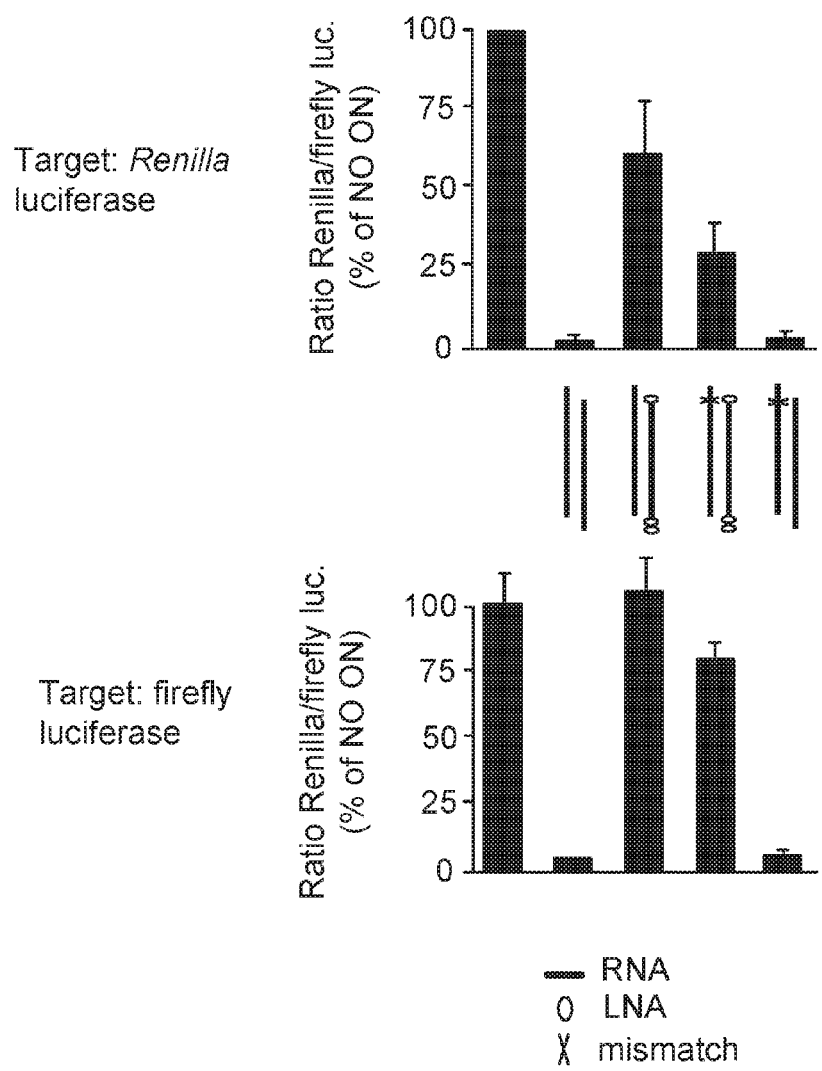
FIG. 11 shows the effect of single base-pair mismatches incorporated opposite to the 5' end of the antisense strand. Lines are RNA, circles indicate LNA monomers and crosses illustrate mismatch incorporations. The tested compounds were (from left to right): *Renilla* luciferase: 2nd bar: RL+/−; 3rd bar: RL+/2701-1; 4th bar: RL+(pos. 19A→C)/2701-1; 5th bar: RL+(pos. 19→C)/−; Firefly Luciferase: 2nd bar: GL3+/−; 3rd bar: GL3+/2187; 4th bar: GL3+(pos. 19A→C)/2187; 5th bar: GL3+(pos. 194-3C)/−.

The effect of incorporating LNA-monomers in the 5' end of the antisense strand can be seen from FIG. 11. The RNAi-impeding effect of a LNA residue in the 5'-end can partially be removed by incorporating an opposite mismatch. In FIG. 11 this has been shown for both the *Renilla* and Firefly targets.

Figure 12:
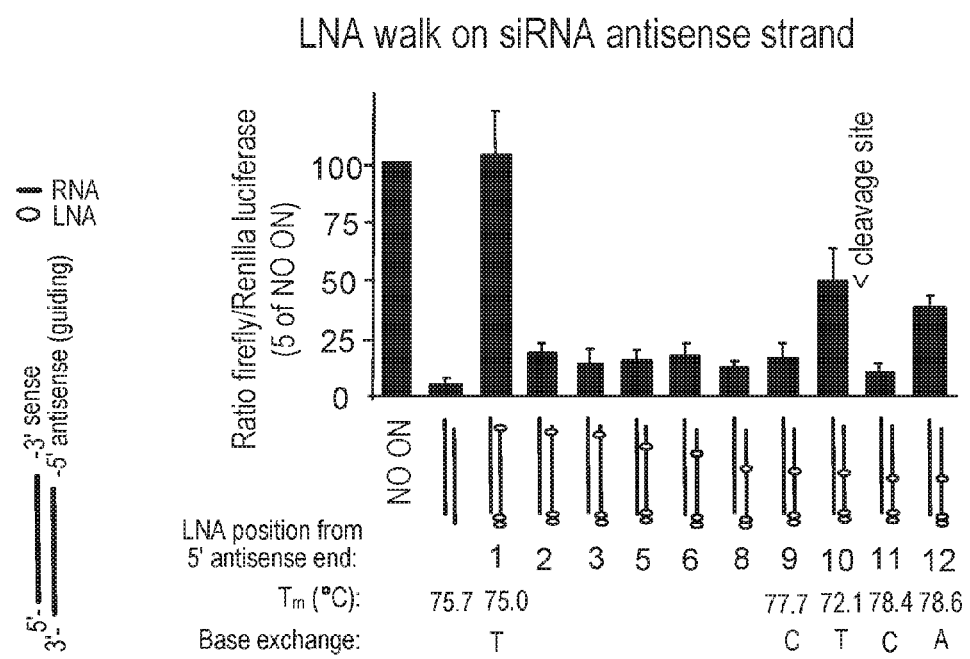
FIG. 12 shows the effect of LNA monomer position in the antisense strand. Lines are RNA, circles indicate LNA monomers. The tested compounds were (from left to right): 2nd bar: GL3+/−; 3rd bar: GL3+/2187; 4th bar: GL3+/2789; 5th bar: GL3+/2790; 6th bar: GL3+/2792: 7th bar: GL3+/2793; 8th bar: GL3+/2794; 9th bar: GL3+/2864; 10th bar: GL3+/2865; 11th bar: GL3+/2866; 12th bar: GL3+/2867.

The RNAi-impeding effect of a LNA monomer incorporated at the 5' end of the antisense strand can be almost eliminated by moving the LNA monomer one base position towards the 3' end (FIG. 12). Moving the LNA-monomer further towards the 3' end of the antisense strand does not affect the gene expression, but when the LNA monomer takes up position 10 or 12 a significant decrease in the RNAi effect is observed. The RISC complex will cleave the mRNA at a position opposite the position between 10 and 11 of the antisense strand of the siRNA and, apparently, incorporation of the synthetic LNA monomer at that site impedes the cleavage by the RISC complex. When the LNA monomer is moved further along the antisense strand this impeding effect is decreased.

Figure 13:
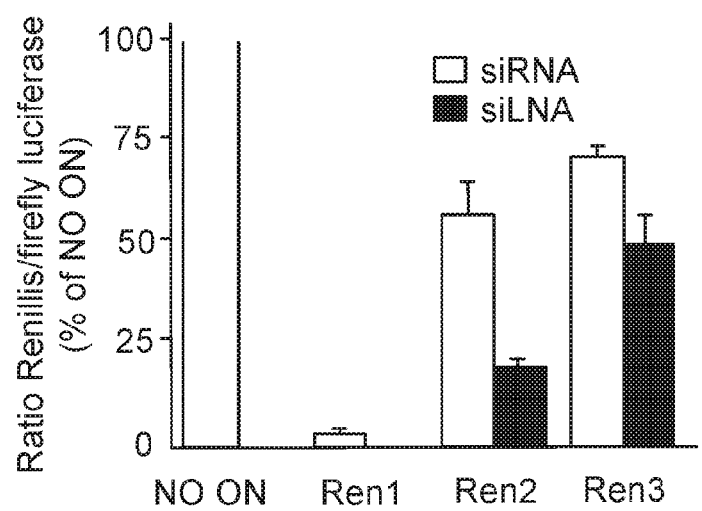
FIG. 13 shows the siLNA improvement of medium-efficient target sites. MOCK represents no oligo. Rent is the optimal target site for siRNA and Ren2 and Ren3 are less potent sites. Lines are RNA and circles indicate LNA monomers. The tested compounds were: Ren1: RL+/−; Ren2: 2863/corresponding unmodified antisense strand; Ren3: 2826/corresponding unmodified antisense strand, as well as the corresponding unmodified siRNAs.
Figure 14:
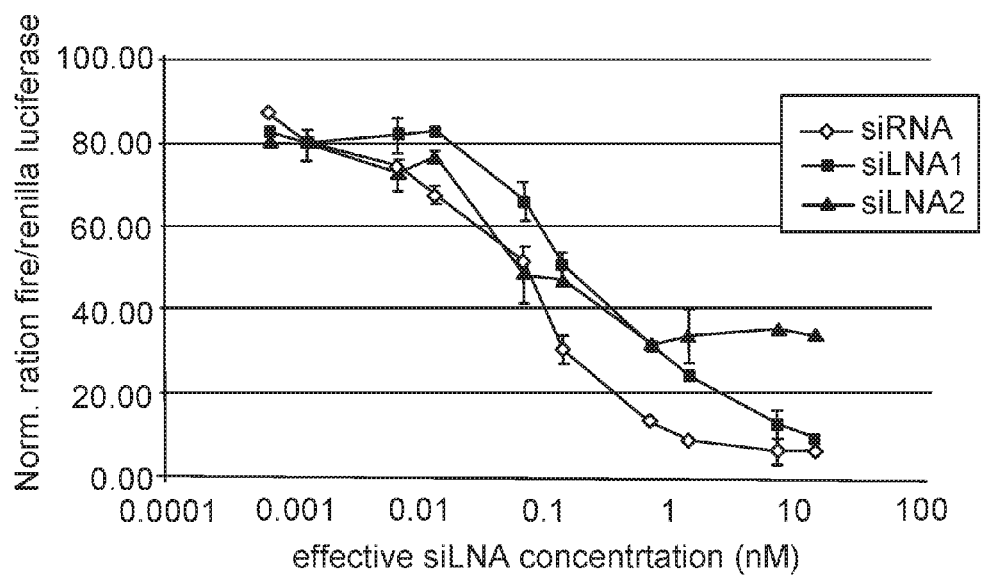
FIG. 14 shows the concentration-depending gene silencing effect of siLNA and siRNA.

As described above the helicase exhibits strand bias and will preferably incorporate siRNA from the weakest binding end of the siRNA. Therefore, in principle, both strands in the siRNA duplex can be incorporated. This among other properties of the RISC-1-siRNA system will give rise to off-target effects. One way of reducing this is to incorporate the high affinity LNA monomers. For the Ren1 site the 5'-nucleobase in the antisense strand is U that constitutes a "low" binding residue. The RISC complex will therefore read from this side and incorporate the antisense strand (the correct strand). For the Rent and Ren3 sites the 5'-nucleobase is C that constitutes "high" binding sites. For these sites the 5' end of the sense strand is positioned by an A and a U nucleobase that both constitutes "low" binding sites. The RISC can therefore exhibit strand bias in this case and read partially from the sense strand (the wrong strand). By replacing the 5'-adenosine and uridine residues with the corresponding A- and U-LNA residues, the strand bias is removed and the antisense strand is incorporated in the RISC complex (FIG. 13). Accordingly, LNA residues can decrease strand bias and increase the potency of the duplex. The siLNA according to the present invention preferably has an antisense sequence, which has least 70%, more preferably 90-100% sequence identity to the target molecule.

Figure 2:
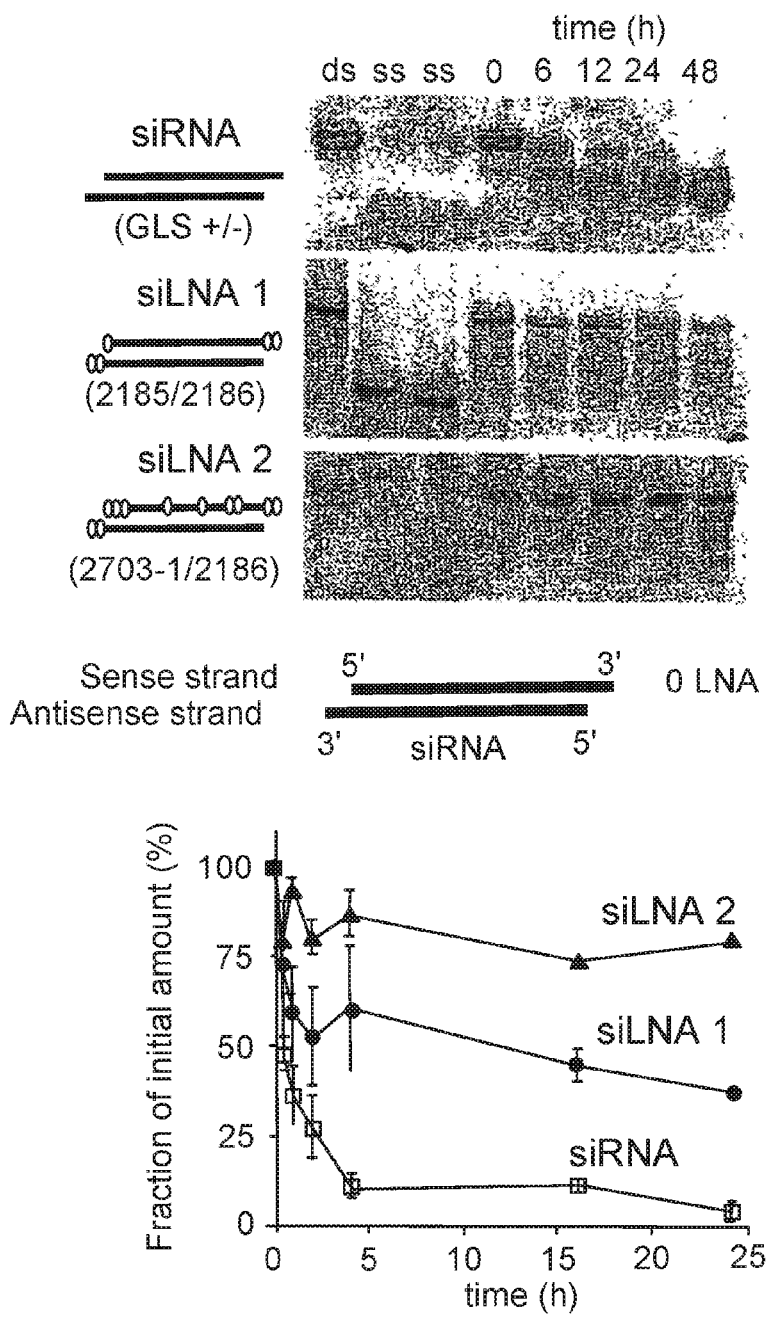
FIG. 2 shows the improved stability of siLNA over siRNA in biological fluids. GL3+/− is rapidly degraded while slightly modified siLNA (No. 2185/2186) and more heavily modified siLNA (No. 2703-01/2186) exhibit a markedly improved stability. The stability study was performed in 10% foetal bovine serum in physiological salt solution at 37° C.
Figure 15:
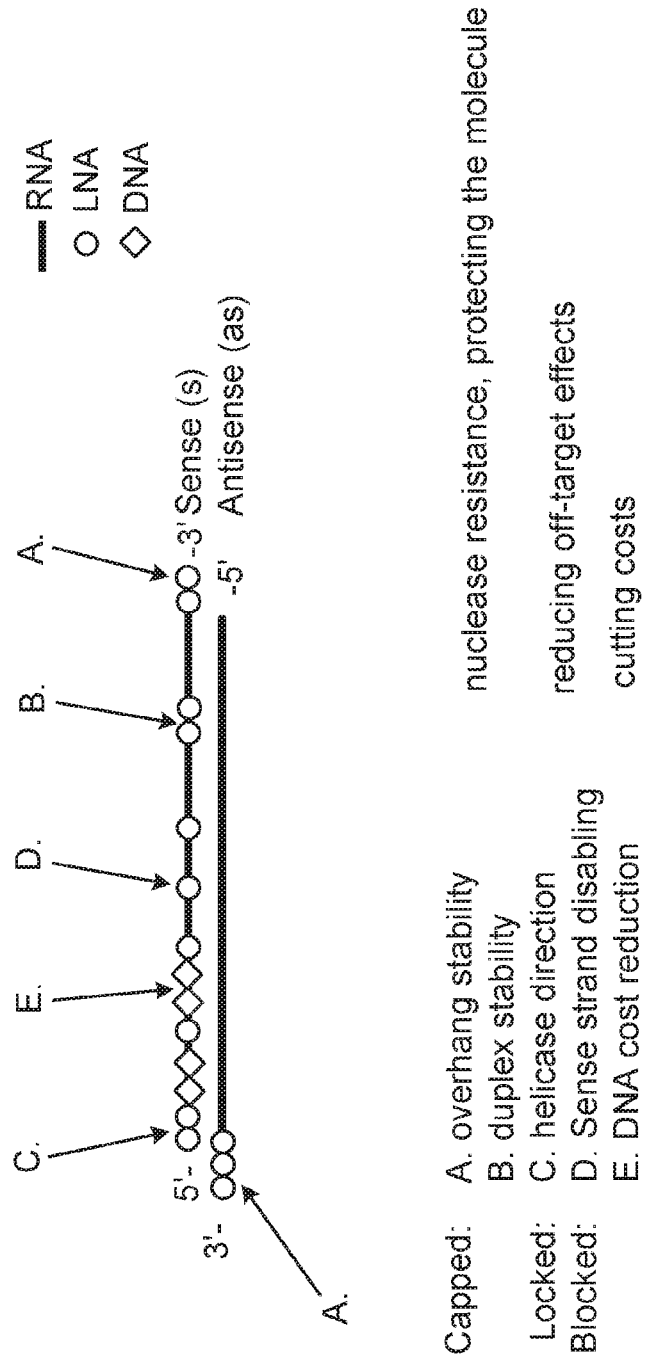
FIG. 15 shows improved designs of modified siRNAs by incorporation of DNA and LNA monomers.

As indicated above several particular designs augment the overall potency applicability of native siRNA:
  (a) "end capping" of the siRNA with LNA improves the nuclease stability (FIGS. 2 and 15).
  (b) Placing a LNA monomer towards the 5'-end of the sense strand improves the potency of the siLNA compared to native siRNA ("locking"). This is illustrated by the potency increase for medium efficient targets (FIGS. 13 and 15).
  (c) In the "LNA walk" (FIG. 12) it is shown that placing a LNA monomer at the cleavage site of the RISC complex, e.g. at position 10, calculated from the 5' end in the antisense strand, decreases the activity of the siRNA ("blocking").

These basic observations are important for improving the overall potency of siRNA. In optimised designs the 3' ends should be "capped" with LNA monomers thereby securing nuclease resistance (FIGS. 12 and 15). The 5' end of the sense strand should also be LNA modified to increase binding to the antisense strand and thereby direct the helicase to incorporate from the "correct side" of the duplex. Such "locking" of the sense 5' end sense/antisense 3' side of the duplex can be done by incorporating at least one LNA monomer at either side of the duplex. Such modified duplexes may also contain LNA-LNA hydrogen bonding bases. The observation that gene silencing is reduced when LNA is incorporated in position 10 or 12 in the antisense strand can be used in the reversed scenario. If the RISC complex should incorporate part of the sense strand and thereby lead to unwanted off-target effects the potency of the unwanted incorporation could be reduced by incorporating LNA at position 10 and 12 in the sense strand ("blocking") as shown in FIG. 12.

Accordingly, in an interesting embodiment of the invention, the sense strand comprises at least one LNA monomer located in at least one (such as one) of the positions 9-13, counted from the 5' end. Preferably, the sense strand comprises at least one LNA monomer located in at least one (such as one) of the positions 10-12, counted from the 5' end. In a particular interesting embodiment of the invention the sense strand comprises a LNA monomer in position 10, position 12 or in both of position 10 and 12, counted from the 5' end. Furthermore, it is particularly preferred that the LNA monomer, if incorporated in position 10, contains a nitrogenous base which is different from the naturally-occurring RNA bases, i.e. different from A, C, G and U. In a particular preferred embodiment the LNA monomer located at position 10 (counted from the 5' end) contains the nitrogenous base T.

It is known that LNA monomers incorporated into oligos will induce a RNA-like structure of the oligo and the hybrid that it may form. It has also been shown that LNA residues modify the structure of DNA residues, in particular when the LNA residues is incorporated in the proximity of 3' end. LNA monomer incorporation towards the 5' end seems to have a smaller effect. This means that it is possible to modify RNA strands which contain DNA monomers, and if one or more LNA residues flank the DNA monomers they too will attain a RNA-like structure. Therefore, DNA and LNA monomer can replace RNA monomers and still the oligo will attain an overall RNA-like structure. As DNA monomers are considerably cheaper than RNA monomers, easier to synthesise and more stable towards nucleolytic degradation, such modifications will therefore improve the overall use and applicability of siRNAs (see, e.g., FIG. 15).

Accordingly, it is preferred that at least one (such as one) LNA monomer is located at the 5' end of the sense strand. More preferably, at least two (such as two) LNA monomers are located at the 5' end of the sense strand.

In another preferred embodiment of the invention, the sense strand comprises at least one (such as one) LNA monomer located at the '3 end of the sense strand. More preferably, at least two (such as two) LNA monomers are located at the 3' end of the of the sense strand.

In a particular preferred embodiment of the invention, the sense strand comprises at least one (such as one) LNA monomer located at the 5' end of the sense strand and at least one (such as one) LNA monomer located at the 3' end of the sense strand. Even more preferably, the sense strand comprises at least two (such as two) LNA monomers located at the 5' end of the sense strand and at least two (such as two) LNA monomers located at the 3' of the sense strand.

It is preferred that at least one (such as one) LNA monomer is located at the 3' end of the antisense strand. More preferably, at least two (such as two) LNA monomers are located at the 3' end of the antisense strand. Even more preferably, at least three (such as three) LNA monomers are located at the 3' end of the antisense strand. In a particular preferred embodiment of the invention, no LNA monomer is located at or near (i.e. within 1, 2, or 3 nucleotides) the 5' end of the antisense strand.

Thus, in a further embodiment of the invention, the LNA monomer may be located in any position of the sense and antisense strands, except for the '5 end of the antisense strand.

In a highly preferred embodiment of the invention, the sense strand comprises at least one LNA monomer at the 5' end and at least one LNA monomer at the 3' end, and the antisense strand comprises at least one LNA monomer at the 3' end. More preferably, the sense strand comprises at least one LNA monomer at the 5' end and at least one LNA monomer at the 3' end, and the antisense strand comprises at least two LNA monomers at the 3' end. Even more preferably, the sense strand comprises at least two LNA monomers at the 5' end and at least two LNA monomers at the 3' end, and the antisense strand comprises at least two LNA monomers at the 3' end. Still more preferably, the sense strand comprises at least two LNA monomers at the 5' end and at least two LNA monomers at the 3' end, and the antisense strand comprises at least three LNA monomers at the 3' end. It will be understood that in the most preferred embodiment, none of the above-mentioned compounds contain a LNA monomer which is located at the 5' end of the antisense strand.

In a further interesting embodiment of the invention, the LNA monomer is located close to the 3' end, i.e. at position 2, 3 or 4, preferably at position 2 or 3, in particular at position 2, calculated from the 3' end.

Accordingly, in a further very interesting embodiment of the invention, the sense strand comprises a LNA monomer located at position 2, calculated from the 3' end. In another embodiment, the sense strand comprises LNA monomers located at position 2 and 3, calculated from the 3' end.

In a particular preferred embodiment of the invention, the sense strand comprises at least one (such as one) LNA monomer located at the 5' end and a LNA monomer located at position 2 (calculated from the 3' end). In a further embodiment, the sense strand comprises at least two (such as two) LNA monomers located at the 5' end of the sense strand a LNA monomer located at positions 2 (calculated from the 3' end).

Furthermore, it is preferred that the antisense strand comprises a LNA monomer at position 2, calculated from the 3' end. More preferably, the antisense strand comprises LNA monomers in position 2 and 3, calculated from the 3' end. Even more preferably, the antisense strand comprises LNA monomers located at position 2, 3 and 4, calculated from the 3' end. In a particular preferred embodiment of the invention, no LNA monomer is located at or near (i.e. within 1, 2, or 3 nucleotides) the 5' end of the antisense strand.

In a highly preferred embodiment of the invention, the sense strand comprises at least one LNA monomer at the 5' end and a LNA monomer at position 2 (calculated from the 3' end), and the antisense strand comprises a LNA monomer located at position 2 (calculated from the 3' end). More preferably, the sense strand comprises at least one LNA monomer at the 5' end and a LNA monomer at position 2 (calculated from the 3' end), and the antisense strand comprises LNA monomers at position 2 and 3 (calculated from the 3' end). Even more preferably, the sense strand comprises at least two LNA monomers at the 5' end and LNA monomers at position 2 and 3 (calculated from the 3' end), and the antisense strand comprises LNA monomers at position 2 and 3 (calculated from the 3' end). Still more preferably, the sense strand comprises at least two LNA monomers at the 5' end and LNA monomers at position 2 and 3 (calculated from the 3' end), and the antisense strand comprises LNA monomers at position 2, 3 and 4 (calculated from the 3' end). It will be understood that in the most preferred embodiment, none of the above-mentioned compounds contain a LNA monomer which is located at the 5' end of the antisense strand.

As indicated above, each strand comprises 12-35 nucleotides. It will be understood that these numbers refer to the total number of naturally occurring nucleotides, nucleotide variants and analogues, LNA monomers, etc., in the strand. Thus, the total number of such naturally occurring nucleotides, nucleotide variants and analogues, LNA monomers, etc., will not be lower than 12 and will not exceed 35. In an interesting embodiment of the invention, each strand comprises 17-25 nucleotides, such as 20-22 or 20-21 nucleotides.

The compounds according to the invention may be blunt ended, and in one particular embodiment the siLNA compound of the invention is a 19-mer and blunt ended. More preferably, however, at least one of the strands has a 3' overhang. Typically, the 3' overhang will be of 1-7 nucleotides (or nucleotide variants or analogues or LNA monomers), preferably of 1-3 nucleotides. Thus, it will be understood that the sense strand may contain a 3' overhang, the antisense strand may contain a 3' overhang, or both of the sense and antisense strands may contain 3' overhangs.

In a similar way, at least one of the strands may have a 5' overhang. Typically, the 5' overhang will be of 1-4 nucleotides (or nucleotide variants or analogues or LNA monomers), preferably of 1-3 nucleotides. Thus, it will be understood that the sense strand may contain a 5' overhang, the antisense strand may contain a 5' overhang, or both of the sense and antisense strands may contain 5' overhangs. Evidently, the sense strand may contain both a 3' and a 5' overhang. Alternatively, the antisense strand may contain both a 3' and a 5' overhang.

Typically, the compounds of the invention will contain other residues than LNA monomers. Such other residues may be any of the residues discussed in connection with the definition of "nucleotide" above, and include, for example, native RNA monomers, native DNA monomers as well as nucleotide variants and analogues such as those mentioned in connection with the definition of "nucleotide" above. Specific examples of such nucleotide variants and analogues include, 2'-F, 2'-O-Me, 2'-O-methoxyethyl (MOE), 2'-O-(3-aminopropyl) (AP), hexitol nucleic acid (HNA), 2'-F-arabino nucleic acid (2'-F-ANA) and D-cyclohexenyl nucleoside (CeNA). Furthermore, the internucleoside linkage may be a phosphorodiester, phosphorothioate or N3'-P5' phosphoroamidate internucleoside linkages as described above.

In general, the individual strands of the compounds of the invention will contain at least about 5%, at least about 10%, at least about 15% or at least about 20% LNA monomer, based on total number of nucleotides in the strand. In certain embodiments, the compounds of the invention will contain at least about 25%, at least about 30%, at least about 40%, at least about 50%, at least about 60%, at least about 70%, at least about 80% or at least about 90% LNA monomer, based on total number of nucleotides in the strand.

As far as the LNA monomers are concerned, it will be understood that any of the LNA monomers shown in Scheme 2 and 3 are useful for the purposes of the present invention.

However, it is currently preferred that the LNA monomer is in the beta-D form, corresponding to the LNA monomers shown as compounds 3A, 3C and 3D. The currently most preferred LNA monomer is the monomer shown as compound 3A in Scheme 3 and 4 above, i.e. the currently most preferred LNA monomer is the beta-D form of oxy-LNA.

In a further embodiment of the invention, the compound of the invention is linked to one or more ligands so as to form a conjugate. The ligand(s) serve(s) the role of increasing the cellular uptake of the conjugate relative to the non-conjugated compound. This conjugation can take place at the terminal 5'-OH and/or 3'-OH positions, but the conjugation may also take place at the sugars and/or the nucleobases. In particular, the growth factor to which the antisense oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/ligands are cholesterol moieties, duplex intercalators such as acridine, poly-L-lysine, "end-capping" with one or more nuclease-resistant linkage groups such as phosphoromonothioate, and the like.

The preparation of transferrin complexes as carriers of oligonucleotide uptake into cells is described by Wagner et al, Proc. Natl. Acad. Sci. USA 87, 3410-3414 (1990). Cellular delivery of folate-macromolecule conjugates via folate receptor endocytosis, including delivery of an antisense oligonucleotide, is described by Low et al, U.S. Pat. No. 5,108, 921 and by Leamon et al., Proc. Natl. Acad. Sci. 88, 5572 (1991).

The compounds or conjugates of the invention may also be conjugated or further conjugated to active drug substances, for example, aspirin, ibuprofen, a sulfa drug, an antidiabetic, an antibacterial agent, a chemotherapeutic agent or an antibiotic.

Figure 16:
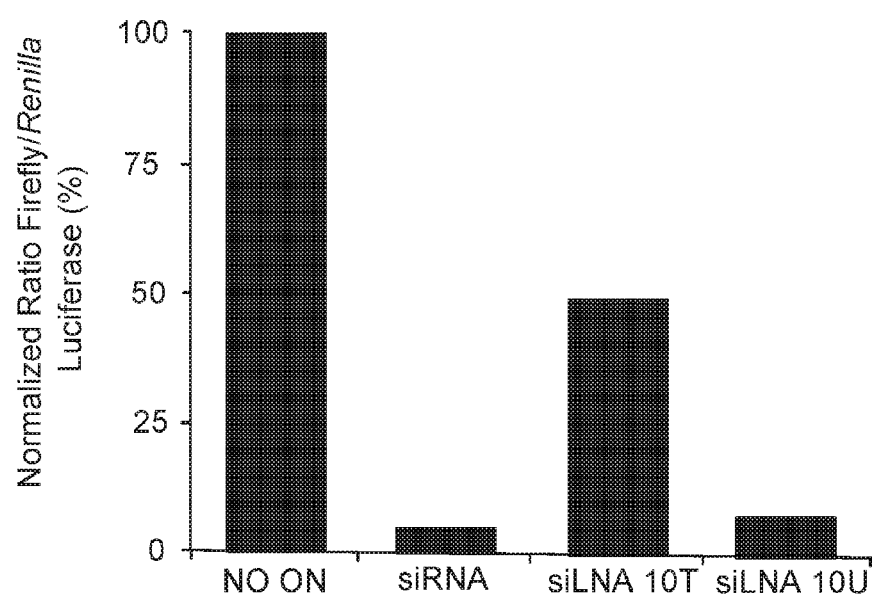
FIG. 16 shows the decreased siLNA efficacy by using a LNA monomer with a bulky nucleobase (T instead of U) at cleaving position 10 in the antisense strand. The tested compounds were: siRNA: GL3+/−; siLNA10T: GL3+/2865; siLNA10U: GL3+/2865-U.
Figure 17:
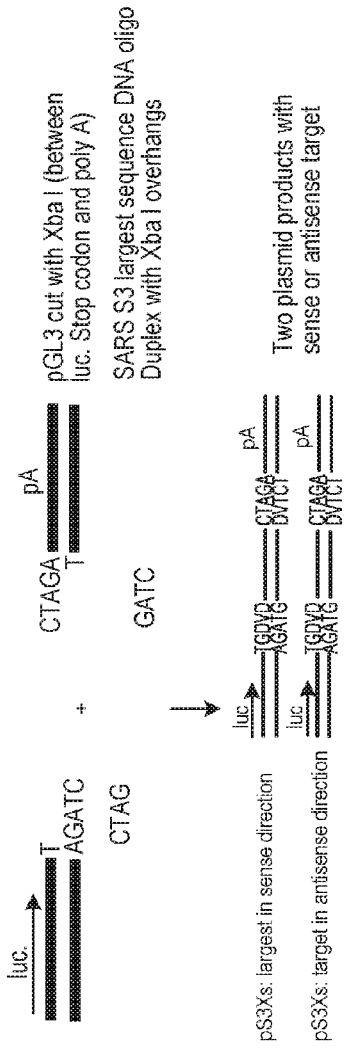
FIG. 17 shows the inhibition of SARS sense/antisense target in 3'-UTR of firefly luciferase
Figure 19:
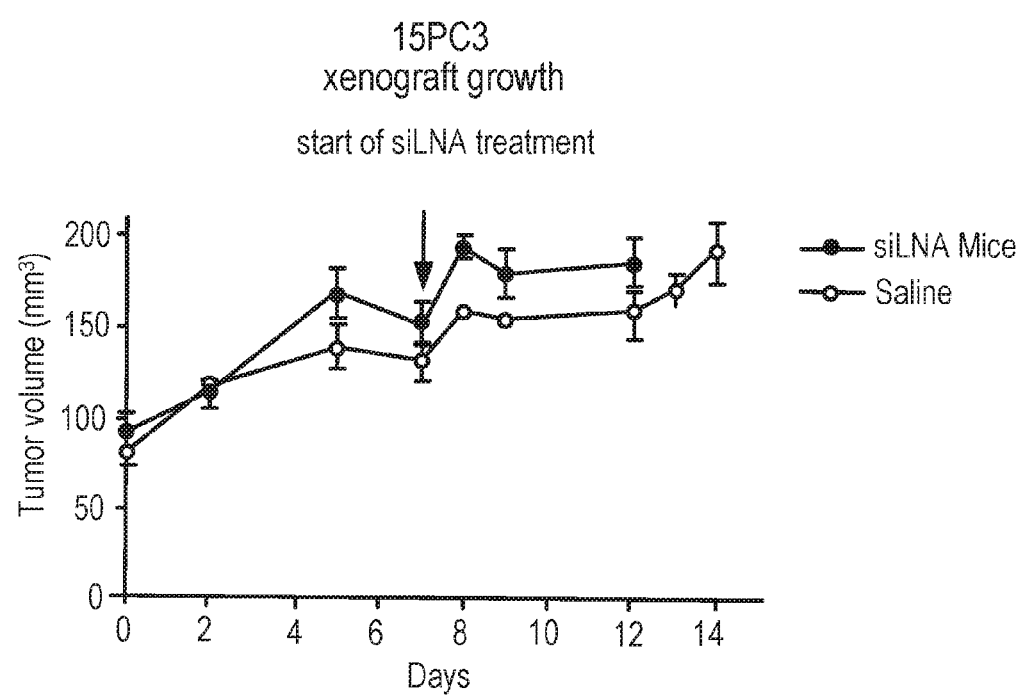
FIG. 19 shows the tumour volume of siLNA- and -saline treated 15PC3-EGFP xenograft NMRI mice using Alzet 1007D minipumps. The tumours were implemented at day 0. The treatment was initiated on day 7 and terminated on day 12. As can be seen, the siLNA-treated mice had a tumour size corresponding to the control mice.
Figure 20:
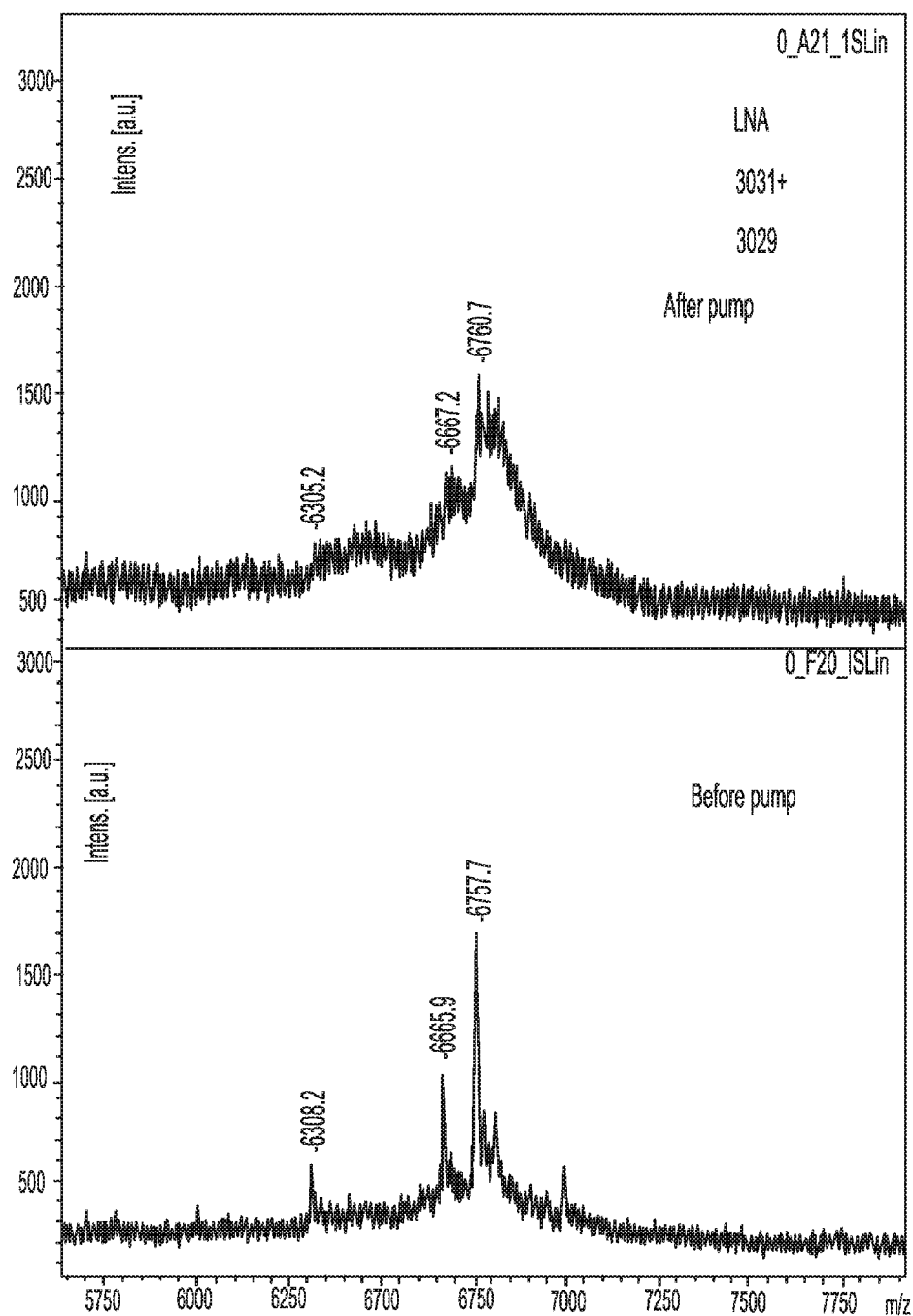
FIG. 20 shows that siLNA duplexes are intact after 7 day in Alzet 1007D minipumps.
Figure 20:
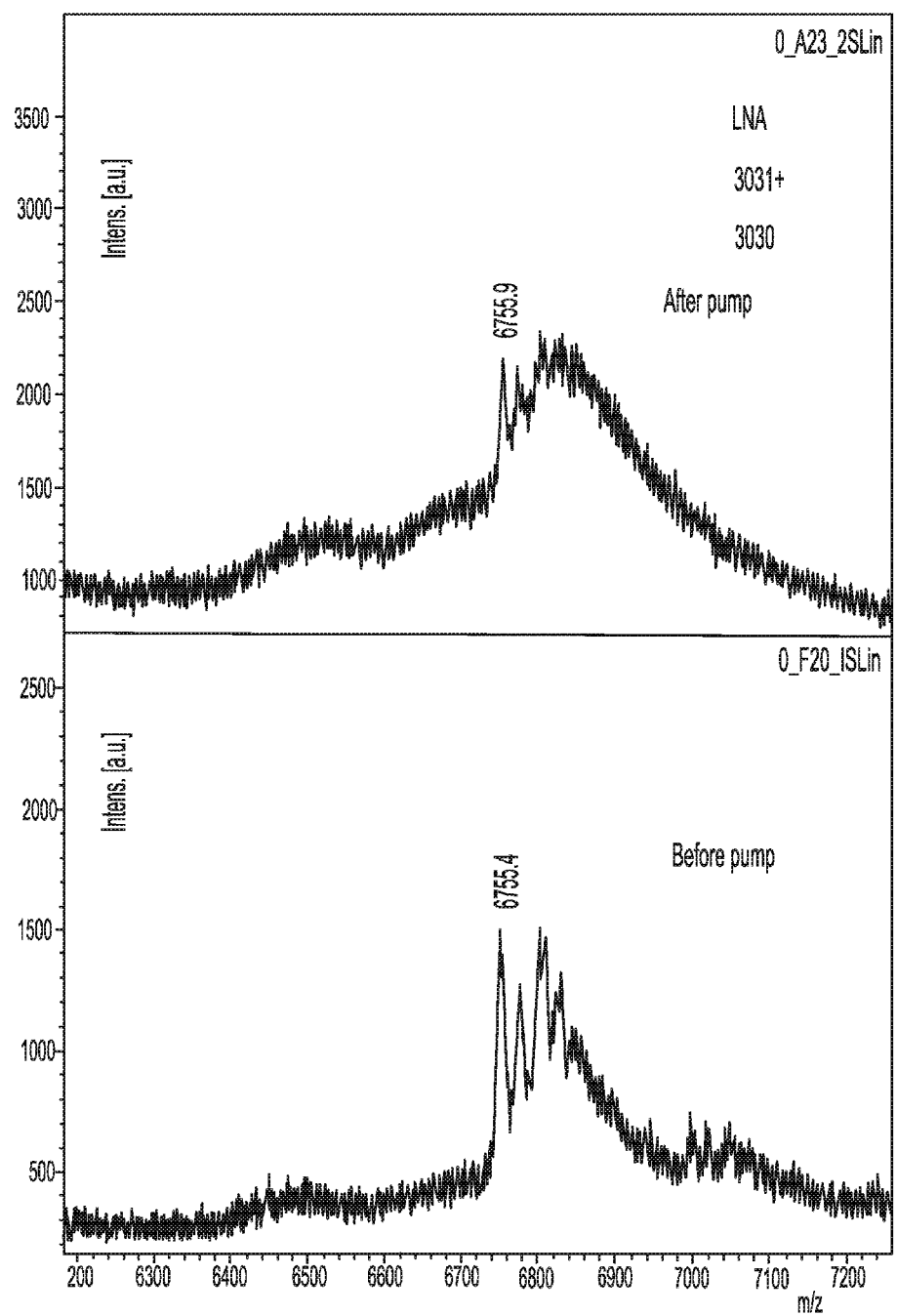

The native RNA nuclebases are A, C, G and U. Using these in LNA monomers will constitute a minimal modification. However, the bases $^{Me}C$ (5' methyl cytosine) and T (thymine) are readily used as LNA monomers and can also be used in siLNA duplexes as shown herein (see FIG. 16). It is anticipated that the nature of the bases used in the ends of the siLNA will not significantly affect the functionality of the siRNA molecule as along as they maintain their ability to hybridize to complementary bases if they occupy a base paired position in the molecule. However, when the LNA modifications are placed at internal positions of the duplex, e.g. at position 10 (calculated from the 5' end), it must be anticipated that the nature of the nucleobase is important. Thus, the native bases, C and U, will perturbe the duplex to a smaller degree than the base modifications, T and $^{Me}C$. This provides subtle design possibilities. For instance if it is wanted to "block" the sense strand in the cleavage site e.g. at the 10th position T or $^{Me}C$ should be used (if complementary), but if it is needed to modify the antisense strand at the cleavage site e.g. position 10 U or C should be used (if complementary). One embodiment of the invention is therefore to include a modified nucleobase. An impediment of the nucleobase could be obtained by using bulkier groups than methyl, e.g. ethyl, propyl, phenyl or reporter groups like biotin. Thus, the differentiated recognition of the nucleobases by the RISC complex, or other enzymes provides an extra level of design opportunities of LNA modified siRNA. Accordingly, in an interesting embodiment of the invention, position 10 (calculated from the 5' end) comprises T or $^{Me}C$.

In order to enable a rapid response to environmental and other changes, biological systems are typically constructed as dynamic systems, i.e. as systems in which the equilibrium state is maintained by the action of both activators and deactivators. Concerning the RISC complex it may therefore be anticipated that the activated complex (i.e. the protein complex containing the intact oligonucleotide that catalyses the destruction of the target) is subject to a deactivating activity, such as for instance a nuclease activity that removes all or part of the oligonucleotide thereby disabling the function of the activated RISC complex. Alternatively, deactivation of the RISC complex may simply be determined by the off-rate of the oligonucleotide from the RISC complex, which, after dissociation, may not be able to re-associate.

Accordingly, in one interesting aspect the present invention relates to the use of the compounds disclosed herein for enhancing the life-time of the active RISC complex thereby enhancing its duration-of-action. In one embodiment of the invention this is achieved by increasing the resistance of the RNA component of the RISC complex to degradation by the putative RNAse activity(ies) by incorporation of LNA and/or other nucleic acids analogues and/or by chemical modifications. In another embodiment of the invention the desired enhancement of the life-time of the active RISC complex is achieved by decreasing the off-rate of the RNA oligonucleotide from the RISC complex through introduction of LNA and/or other nucleic acid analogues and/or by chemical modifications that increases the affinity of the oligonucleotide for its binding partners in the RISC complex.

When designed as an inhibitor, the siLNAs of the invention bind to the target nucleic acid and modulate the expression of its cognate protein. Preferably, such modulation produces an inhibition of expression of at least 10% or at least 20% compared to the normal expression level, more preferably at least 30%, at least 40%, at least 50%, at least 60%, at least 70%, at least 80%, or at least 90% inhibition compared to the normal expression level.

Manufacture

The compounds of the invention may be produced using the polymerisation techniques of nucleic acid chemistry, which is well known to a person of ordinary skill in the art of organic chemistry. Generally, standard oligomerisation cycles of the phosphoramidite approach (S. L. Beaucage and R. P. Iyer, Tetrahedron, 1993, 49, 6123; and S. L. Beaucage and R. P. Iyer, Tetrahedron, 1992, 48, 2223) may be used, but other chemistries, such as the H-phosphonate chemistry or the phosphortriester chemistry may also be used.

For some monomers longer coupling time and/or repeated couplings with fresh reagents and/or use of more concentrated coupling reagents may be necessary. However, in our hands, the phosphoramidites employed coupled with a satisfactory >97% step-wise coupling yield. Thiolation of the phosphate may be performed by exchanging the normal oxidation, i.e. the iodine/pyridine/$H_2O$ oxidation, with an oxidation process using Beaucage's reagent (commercially available). As will be evident to the skilled person, other sulphurisation reagents may be employed.

Purification of the individual strands may be done using disposable reversed phase purification cartridges and/or reversed phase HPLC and/or precipitation from ethanol or butanol. Gel electrophoresis, reversed phase HPLC, MALDI-MS, and ESI-MS may be used to verify the purity of the synthesised LNA-containing oligonucleotides. Furthermore, solid support materials having immobilised thereto a nucleobase-protected and 5'-OH protected LNA are especially interesting for synthesis of the LNA-containing oligonucleotides where a LNA monomer is included at the 3' end. For this purpose, the solid support material is preferable CPG or polystyrene onto which a 3'-functionalised, optionally nucleobase protected and optionally 5'-OH protected LNA monomer is linked. The LNA monomer may be attached to the solid support using the conditions stated by the supplier for that particular solid support material.

One aspect of the present invention is directed to a novel method for synthesis of the compounds of the invention, which is characterised in that the individual monomers, e.g. the LNA monomers and RNA monomers, are coupled using 1H-tetrazole or 5-ethylthio-1H-tetrazole. A further embodiment of this aspect is that the method involves a coupling time which is in the range of 200-1200 second, such as in the range of 400-1200 seconds, preferably in the range of 600-900 seconds.

The targets to be modified according to the present invention may be targets involved in a number of basic biological mechanisms including red blood cell proliferation, cellular proliferation, ion metabolism, glucose and energy metabolism, pH regulation and matrix metabolism. The invention described herein encompasses a method of preventing or treating cancer comprising a therapeutically effective amount of a target modulating siRNA compound to a human in need of such therapy.

Therapy and Pharmaceutical Compositions

As explained initially, the compounds of the invention will constitute suitable drugs with improved properties. The design of a potent and safe RNAi drug requires the fine-tuning of diverse parameters such as affinity/specificity, stability in biological fluids, cellular uptake, mode of action, pharmacokinetic properties and toxicity.

Accordingly, in a further aspect the present invention relates to a pharmaceutical composition comprising a compound according to the invention and a pharmaceutically acceptable diluent, carrier or adjuvant.

In a still further aspect the present invention relates to a compound according to the invention for use as a medicament.

As will be understood dosing is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual siLNAs. Generally it can be estimated based on EC50s found to be effective in in vitro and in vivo animal models. In general, dosage is from 0.01 μg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

Pharmaceutical Composition

It should be understood that the invention also relates to a pharmaceutical composition, which comprises at least one compound of the invention as an active ingredient. It should be understood that the pharmaceutical composition according to the invention optionally comprises a pharmaceutical carrier, and that the pharmaceutical composition optionally comprises further compounds, such as chemotherapeutic compounds, anti-inflammatory compounds, antiviral compounds and/or immuno-modulating compounds.

The oligomeric compound comprised in this invention can be employed in a variety of pharmaceutically acceptable salts. As used herein, the term refers to salts that retain the desired biological activity of the herein-identified compounds and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine.

In one embodiment of the invention the oligomeric compound may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach the oligonucleotides are prepared in a protected manner so that the oligo is neutral when it is administered. These protection groups are designed in such a way that they can be removed when the oligo is taken up by the cells. Examples of such protection groups are S-acetylthioethyl (SATE) or S-pivaloylthioethyl (t-butyl-SATE). These protection groups are nuclease resistant and are selectively removed intracellularly.

Pharmaceutically acceptable binding agents and adjuvants may comprise part of the formulated drug. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellular emulsion. A compound of the invention may be mixed with any material that do not impair the desired action, or with material that supplement the desired action. These could include other drugs including other nucleotide compounds. For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

Preferably, an oligomeric compound is included in a unit formulation such as in a pharmaceutically acceptable carrier or diluent in an amount sufficient to deliver to a patient a therapeutically effective amount without causing serious side effects in the treated patient.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment the pharmaceutical composition is administered IV, IP, orally, topically or as a bolus injection or administered directly in to the target organ. Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the compounds of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27). The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The compounds of the invention may also be conjugated to active drug substances, for example, aspirin, ibuprofen, a sulfa drug, an antidiabetic, an antibacterial or an antibiotic.

In another embodiment, compositions of the invention may contain one or more siLNA compounds, targeted to a first nucleic acid and one or more additional siLNA compounds targeted to a second nucleic acid target. Two or more combined compounds may be used together or sequentially.

The compounds disclosed herein are useful for a number of therapeutic applications as indicated above. In general, therapeutic methods of the invention include administration of a therapeutically effective amount of a siLNA to a mammal, particularly a human. In a certain embodiment, the present invention provides pharmaceutical compositions containing (a) one or more compounds of the invention, and (b) one or more chemotherapeutic agents. When used with the compounds of the invention, such chemotherapeutic agents may be used individually, sequentially, or in combination with one or more other such chemotherapeutic agents or in combination with radiotherapy. All chemotherapeutic agents known to a person skilled in the art are here incorporated as combination treatments with compound according to the invention. Other active agents, such as anti-inflammatory drugs, including but not limited to nonsteroidal anti-inflammatory drugs and corticosteroids, antiviral drugs, and immuno-modulating drugs may also be combined in compositions of the invention. Two or more combined compounds may be used together or sequentially.

Cancer

In an even further aspect the present invention relates to the use of a compound according to the invention for the manufacture of a medicament for the treatment of cancer. In another aspect the present invention concerns a method for treatment of, or prophylaxis against, cancer, said method comprising administering a compound of the invention or a pharmaceutical composition of the invention to a patient in need thereof.

Such cancers may include lymphoreticular neoplasia, lymphoblastic leukemia, brain tumors, gastric tumors, plasmacytomas, multiple myeloma, leukemia, connective tissue tumors, lymphomas, and solid tumors.

In the use of a compound of the invention for the manufacture of a medicament for the treatment of cancer, said cancer may suitably be in the form of a solid tumor. Analogously, in the method for treating cancer disclosed herein said cancer may suitably be in the form of a solid tumor.

Furthermore, said cancer is also suitably a carcinoma. The carcinoma is typically selected from the group consisting of malignant melanoma, basal cell carcinoma, ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma and carcinoid tumors. More typically, said carcinoma is selected from the group consisting of malignant melanoma, non-small cell lung cancer, breast carcinoma, colon carcinoma and renal cell carcinoma. The malignant melanoma is typically selected from the group consisting of superficial spreading melanoma, nodular melanoma, lentigo maligna melanoma, acral melagnoma, amelanotic melanoma and desmoplastic melanoma.

Alternatively, the cancer may suitably be a sarcoma. The sarcoma is typically in the form selected from the group consisting of osteosarcoma, Ewing's sarcoma, chondrosarcoma, malignant fibrous histiocytoma, fibrosarcoma and Kaposi's sarcoma.

Alternatively, the cancer may suitably be a glioma.

A further embodiment is directed to the use of a compound according to the invention for the manufacture of a medicament for the treatment of cancer, wherein said medicament further comprises a chemotherapeutic agent selected from the group consisting of adrenocorticosteroids, such as prednisone, dexamethasone or decadron; altretamine (hexylen, hexamethylmelamine (HMM)); amifostine (ethyol); aminoglutethimide (cytadren); amsacrine (M-AMSA); anastrozole (arimidex); androgens, such as testosterone; asparaginase (elspar); *bacillus* calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); Idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine). Suitably, the further chemotherapeutic agent is selected from taxanes such as Taxol, Paclitaxel or Docetaxel.

Similarly, the invention is further directed to the use of a compound according to the invention for the manufacture of a medicament for the treatment of cancer, wherein said treatment further comprises the administration of a further chemotherapeutic agent selected from the group consisting of adrenocorticosteroids, such as prednisone, dexamethasone or decadron; altretamine (hexylen, hexamethylmelamine (HMM)); amifostine (ethyol); aminoglutethimide (cytadren); amsacrine (M-AMSA); anastrozole (arimidex); androgens, such as testosterone; asparaginase (elspar); *bacillus* calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine). Suitably, said treatment further comprises the administration of a further chemotherapeutic agent selected from taxanes, such as Taxol, Paclitaxel or Docetaxel.

Alternatively stated, the invention is furthermore directed to a method for treating cancer, said method comprising administering a compound of the invention or a pharmaceutical composition according to the invention to a patient in need thereof and further comprising the administration of a further chemotherapeutic agent. Said further administration may be such that the further chemotherapeutic agent is conjugated to the compound of the invention, is present in the pharmaceutical composition, or is administered in a separate formulation.

Infectious Diseases

Figure 10:
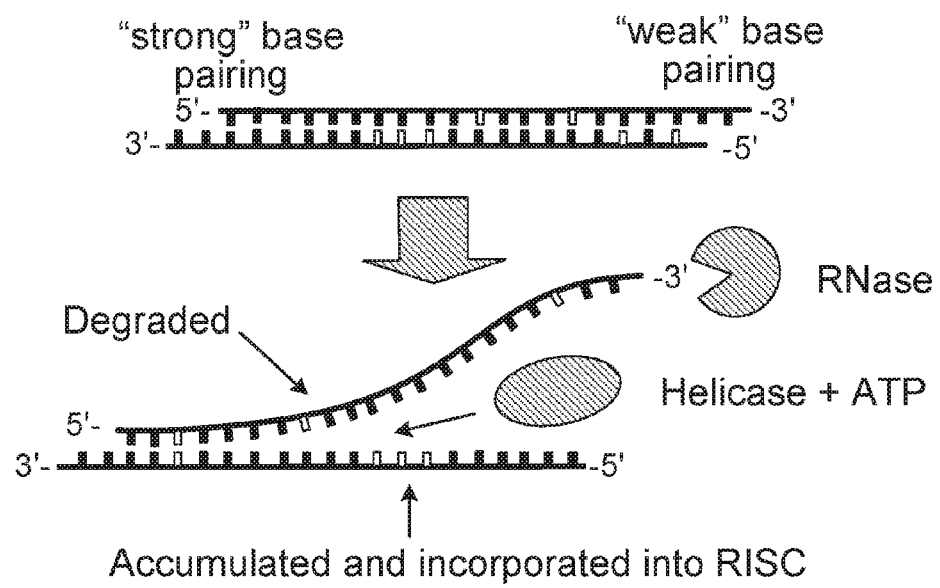
FIG. 10 shows the proposed mechanism of RISC loading where the helicase is unwinding the siRNA duplex at the weakest binding end.

In a particular interesting embodiment of the invention, siLNA compounds according to the invention are used for targeting Severe Acute Respiratory Syndrome (SARS), which first appeared in China in November 2002. According to the WHO over 8,000 people have been infected worldwide, resulting in over 900 deaths. A previously unknown coronavirus has been identified as the causative agent for the SARS epidemic (Drosten C et al. N Engl J Med 2003, 348, 1967-76; and Fouchier R A et al. Nature 2003, 423,240). Identification of the SARS-CoV was followed by rapid sequencing of the viral genome of multiple isolates (Ruan et al. Lancet 2003, 361,1779-85; Rota P A et al. Science 2003, 300,1394-9; and Marra M A et al. Science 2003, 300,399-404). This sequence information immediately made possible the development of SARS antivirals by nucleic acid-based knock-down techniques such as siRNA. The nucleotide sequence encoding the SARS-CoV RNA-dependent RNA polymerase (Pol) is highly conserved throughout the coronavirus family. The Pol gene product is translated from the genomic RNA as a part of a polyprotein, and uses the genomic RNA as a template to synthesize negative-stranded RNA and subsequently sub-genomic mRNA. The Pol protein is thus expressed early in the viral life cycle and is crucial to viral replication (see FIG. 10).

Accordingly, in a further another aspect the present invention relates the use of a compound according to the invention for the manufacture of a medicament for the treatment of Severe Acute Respiratory Syndrome (SARS), as well as to a method for treating Severe Acute Respiratory Syndrome (SARS), said method comprising administering a compound according to the invention or a pharmaceutical composition according to the invention to a patient in need thereof.

It is contemplated that the compounds of the invention may be broadly applicable to a broad range of infectious diseases, such as diphtheria, tetanus, pertussis, polio, hepatitis B, *hemophilus influenza*, measles, mumps, and rubella.

Accordingly, in yet another aspect the present invention relates the use of a compound according to the invention for the manufacture of a medicament for the treatment of an infectious disease, as well as to a method for treating an infectious disease, said method comprising administering a compound according to the invention or a pharmaceutical composition according to the invention to a patient in need thereof.

Inflammatory Diseases

The inflammatory response is an essential mechanism of defense of the organism against the attack of infectious agents, and it is also implicated in the pathogenesis of many acute and chronic diseases, including autoimmune disorders. In spite of being needed to fight pathogens, the effects of an inflammatory burst can be devastating. It is therefore often necessary to restrict the symptomatology of inflammation with the use of anti-inflammatory drugs. Inflammation is a complex process normally triggered by tissue injury that includes activation of a large array of enzymes, the increase in vascular permeability and extravasation of blood fluids, cell migration and release of chemical mediators, all aimed to both destroy and repair the injured tissue.

In yet another aspect, the present invention relates to the use of a compound according to the invention for the manufacture of a medicament for the treatment of an inflammatory disease, as well as to a method for treating an inflammatory disease, said method comprising administering a compound according to the invention or a pharmaceutical composition according to the invention to a patient in need thereof.

In one preferred embodiment of the invention, the inflammatory disease is a rheumatic disease and/or a connective tissue diseases, such as rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris and Sjorgren's syndrome, in particular inflammatory bowel disease and Crohn's disease.

Alternatively, the inflammatory disease may be a non-rheumatic inflammation, like bursitis, synovitis, capsulitis, tendinitis and/or other inflammatory lesions of traumatic and/or sportive origin.

Other Uses

The siRNA compounds of the present invention can be utilized for as research reagents for diagnostics, therapeutics and prophylaxis. In research, the siRNA may be used to specifically inhibit the synthesis of target genes in cells and experimental animals thereby facilitating functional analysis of the target or an appraisal of its usefulness as a target for therapeutic intervention. In diagnostics the siRNA oligonucleotides may be used to detect and quantitate target expression in cell and tissues by Northern blotting, in-situ hybridisation or similar techniques. For therapeutics, an animal or a human, suspected of having a disease or disorder, which can be treated by modulating the expression of target is treated by administering the siRNA compounds in accordance with this invention. Further provided are methods of treating an animal particular mouse and rat and treating a human, suspected of having or being prone to a disease or condition, associated with expression of target by administering a therapeutically or prophylactically effective amount of one or more of the siRNA compounds or compositions of the invention.

The invention is further illustrated in a non-limiting manner by the following examples.

EXAMPLES

Abbreviations

DMT: Dimethoxytrityl
DCI: 4,5-Dicyanoimidazole
DMAP: 4-Dimethylaminopyridine
DCM: Dichloromethane
DMF: Dimethylformamide
THF: Tetrahydrofuran
DIEA: N,N-diisopropylethylamine
PyBOP: Benzotriazole-1-yl-oxy-tris-pyrrolidino-phosphonium hexafluorophosphate
Bz: Benzoyl
Ibu: Isobutyryl
Beaucage: 3H-1,2-Benzodithiole-3-one-1,1-dioxide
GL3+: 5'-cuuacgcugaguacuucga$_d$t$_d$t-3',
GL3−: 5'-ucgaaguacucagcguaag$_d$t$_d$t-3'
NPY+: 5'-ugagagaaagcacagaaaa$_d$t$_d$t-3'
NPY−: 5'-uuuucugugcuuucucuca$_d$t$_d$t-3'
RL+: 5'-aucugaagaaggagaaaaa$_d$t$_d$t-3'
RL−: 5'-uuuuucuccuucuucagau$_d$t$_d$t-3'
Small letters without prefix: RNA monomer
Small letters with "d" prefix: DNA monomer Example 1

Monomer Synthesis

The preparation of LNA monomers is described in great detail in the references Koshkin et al., J. Org. Chem., 2001, 66,8504-8512, and Pedersen et al., Synthesis, 2002, 6,802-809 as well as in references given therein. Where the Z and Z* protection groups were oxy-N,N-diisopropyl-O-(2-cyanoethyl)phosphoramidite and dimethoxytrityloxy such compounds were synthesised as described in WO 03/095467; Pedersen et al., Synthesis 6, 802-808, 2002; Sørensen et al., J. Am. Chem. Soc., 124, 2164-2176, 2002; Singh et al., J. Org. Chem. 63, 6078-6079, 1998; and Rosenbohm et al., Org. Biomol. Chem. 1, 655-663, 2003. All cytosine-containing monomers were replaced with 5-methyl-cytosine monomers for all couplings. All LNA monomers used were beta-D-oxy LNA (compound 3A).

Example 2

Oligonucleotide Synthesis

All syntheses were carried out in 1 μmole scale on a MOSS Expedite instrument platform. The synthesis procedures were carried out essentially as described in the instrument manual.

Preparation of LNA Succinyl Hemiester

5'-O-DMT-3"hydroxy-LNA monomer (500 mg), succinic anhydride (1.2 eq.) and DMAP (1.2 eq.) were dissolved in DCM (35 ml). The reaction mixture was stirred at room temperature overnight. After extraction with $NaH_2PO_4$, 0.1 M, pH 5.5 (2×), and brine (1×), the organic layer was further dried with anhydrous $Na_2SO_4$, filtered, and evaporated. The hemiester derivative was obtained in a 95% yield and was used without any further purification.

Preparation of LNA-CPG (Controlled Pore Glass)

The above-prepared hemiester derivative (90 μmole) was dissolved in a minimum amount of DMF. DIEA and pyBOP (90 μmole) were added and mixed together for 1 min. This pre-activated mixture was combined with LCAA-CPG (500 Å, 80-120 mesh size, 300 mg) in a manual synthesiser and stirred. After 1.5 h stirring at room temperature, the support was filtered off and washed with DMF, DCM and MeOH. After drying the loading was determined to be 57 μmol/g (see Tom Brown, Dorcas J. S. Brown. Modern machine-aided methods of oligodeoxyribonucleotide synthesis. In: F. Eckstein, editor. Oligonucleotides and Analogues A Practical Approach. Oxford: IRL Press, 1991: 13-14).

Phosphorothioate Cycles

5'-O-DMT (A(bz), C(bz), G(ibu) or T) linked to CPG were deprotected using a solution of 3% trichloroacetic acid (v/v) in dichloromethane. The CPG was washed with acetonitrile. Coupling of phosphoramidites (A(bz), G(ibu), 5-methyl-C (bz)) or T-β-cyanoethylphosphoramidite) was performed by using 0.08 M solution of the 5'-O-DMT-protected amidite in acetonitrile and activation was done by using DCI (4,5-dicyanoimidazole) in acetonitrile (0.25 M). The coupling reaction was carried out for 2 min. Thiolation was carried out by using Beaucage reagent (0.05 M in acetonitrile) and was allowed to react for 3 min. The support was thoroughly washed with acetonitrile and the subsequent capping was carried out by using standard solutions (CAP A) and (CAP B) to cap unreacted 5' hydroxyl groups. The capping step was then repeated and the cycle was concluded by acetonitrile washing.

LNA Unit Cycles

5'-O-DMT (A(bz), C(bz), G(ibu) or T) linked to CPG was deprotected by using the same procedure as described above. Coupling was performed by using 5'-O-DMT-A(bz), C(bz), G(ibu) or T-β-cyanoethylphosphoramidite (0.1 M in acetonitrile) and activation was done by DCI (0.25 M in acetonitrile). The coupling reaction was carried out for 7 minutes. Capping was done by using standard solutions (CAP A) and (CAP B) for 30 sec. The phosphite triester was oxidized to the more stable phosphate triester by using a standard solution of $I_2$ and pyridine in THF for 30 sec. The support was washed with acetonitrile and the capping step was repeated. The cycle was concluded by thorough acetonitrile wash.

Cleavage and Deprotection

The oligonucleotides were cleaved from the support and the β-cyanoethyl protecting group removed by treating the support with 35% $NH_4OH$ for 1 h at room temperature. The support was filtered off and the base protecting groups were removed by raising the temperature to 65° C. for 4 hours. Ammonia was then removed by evaporation.

Purification

The oligos were either purified by reversed-phase-HPLC (RP-HPLC) or by anion exchange chromatography (AIE):

RP-HPLC:
   Column: VYDAC™, Cat. No. 218TP1010 (vydac)
   Flow rate: 3 ml/min
   Buffer: A (0.1 M ammonium acetate, pH 7.6)
   B (acetonitrile)

Gradient:

| Time | 0 | 10 | 18 | 22 | 23 | 28 |
|------|---|----|----|----|----|----|
| B %  | 0 | 5  | 30 | 100| 100| 0  |

AIE:
   Column: Resource™ 15Q (amersham pharmacia biotech)
   Flow rate: 1.2 ml/min
   Buffer: A (0.1 M NaOH)
   B (0.1 M NaOH, 2.0 M NaCl)

Gradient:

| Time | 0 | 1  | 27 | 28 | 32 | 33 |
|------|---|----|----|----|----|----|
| B %  | 0 | 25 | 55 | 100| 100| 0  |

Tm Measurement

Melting curves were recorded on a Perkin Elmer UV/VIS spectrophotometer lambda 40 attached to a PTP-6 Peltier System. Oligonucleotides were dissolved in salt buffer (10 mM phosphate buffer, 100 mM NaCl, 0.1 mM EDTA, pH 7.0) at a concentration of 1.5 μM and using 1 cm path-length cells. Samples were denatured at 95° C. for 3 min and slowly cooled to 20° C. prior to measurements. Melting curves were recorded at 260 nm using a heating rate of 1° C./min, a slit of 2 nm and a response of 0.2 sec. Tm values were obtained from the maximum of the first derivative of the melting curves.

Example 3

Synthesis of LNA/RNA Oligonucleotides

Synthesis

LNA/RNA oligonucleotides were synthesized DMT-off on a 1.0 μmole scale using an automated nucleic acid synthesiser (MOSS Expedite 8909) and using standard reagents. 1H-tetrazole or 5-ethylthio-1H-tetrazole were used as activators. The LNA $A^{Bz}$, $G^{iBu}$ and T phosphoramidite concentration was 0.1 M in anhydrous acetonitrile. The $^{Me}C^{Bz}$ was dissolved in 15% THF in acetonitrile. The coupling time for all monomer couplings was 600 secs. The RNA phosphoramidites (Glen Research, Sterling, Va.) were N-acetyl and 2'-O-triisopropylsilyloxymethyl (TOM) protected. The monomer concentration was 0.1 M (anhydrous acetonitrile) and the coupling time was 900 secs. The oxidation time was set to be 50 sec. The solid support was DMT-LNA-CPG (1000 Å, 30-40 μmole/g)

Work-Up and Purification

Cleavage from the resin and nucleobase/phosphate deprotection was carried out in a sterile tube by treatment with 1.5 ml of a methylamine solution (1:1, 33% methylamine in ethanol:40% methylamine in water) at 35° C. for 6 h or left overnight. The tube was centrifuged and the methylamine solution was transferred to second sterile tube. The methylamine solution was evaporated in a vacuum centrifuge. To remove the 2'-β-protection groups the residue was dissolved in 1.0 ml 1.0 M TBAF in THF and heated to 55° C. for 15 min. and left at 35° C. overnight. The THF was evaporated in a vacuum centrifuge leaving a light yellow gum, which was neutralised with approx. 600 μl (total sample volume: 1.0 ml) of RNase-free 1.0 M Tris-buffer (pH 7). The mixture was homogenised by shaking and heating to 65° C. for 3 min. Desalting of the oligonucleotides was performed on NAP-10 columns (Amersham Biosciences, see below). The filtrate from step 4 (see below) was collected and analysed by MALDI-TOF and gel electroforesis (16% sequencing acrylamide gel (1 mm), 0.9% TBE [Tris: 89 mM, Boric acid: 89 mM, EDTA: 2 mM, pH 8.3] buffer, ran for 2 h at 20 W as the limiting parameter. The gel was stained in CyberGold (Molecular Probes, 1:10000 in 0.9×TBE) for 30 min followed by scanning in a Bio-Rad FX Imager). The concentration of the oligonucleotide was measured by UV-spectrometry at 260 nm.

Scheme A, Desalting on NAP-10 Columns:

| Step | Reagent | Operation | Volume | Remarks |
|---|---|---|---|---|
| 1 | — | Empty storage buffer | — | Discard |
| 2 | H$_2$O (RNase-free) | Wash | 2 × full volume | Discard |
| 3 | Oligo in buffer (RNase-free) | Load | 1.0 ml | Discard |
| 4 | H$_2$O (RNase-free) | Elution | 1.5 ml | Collect - Contains oligo |
| 5 | H$_2$O (RNase-free) | "Elution" | 0.5 ml | Collect - Contains salt + small amount of oligo |

As will be appreciated by the skilled person, the most important issues in the synthesis of the LNA/RNA oligos as compared to standard procedures are that i) extended coupling times are necessary to achieve good coupling efficiency, and ii) the oxidation time has to be extended to minimise the formation of deletion fragments. Furthermore, coupling of 2'-O-TOM protected phosphoramidites were superior to 2'-O-TBDMS. Taking this into account, the crude oligonucleotides were of such quality that further purification could be avoided. MS analysis should be carried out after the TOM-groups are removed.

Example 4

Improved Stability of siRNA as Compared to siRNA

The improved stability of siLNA as compared to siRNA is shown in FIG. 2. Both slightly- and more heavily-modified siRNA exhibited improved stability. Stability was evaluated in 10% foetal bovine serum diluted in a physiological saline solution. The siRNA and siLNA were incubated in the serum at 37° C. Samples were withdrawn at different time points and analysed on 15% polyacrylamide TBE gels and stained with SYBR-gold (Molecular probes). Bands were quantified and plotted in a graph. For the unmodified siRNA compound an accumulation of an intermediate band can be seen (inbetween dsRNA and ssRNA) that has been identified to be a doublestranded 19-mer, i.e. siRNA with degraded 3' overhangs. This was not observed for the corresponding siLNAs.

Example 5

Test of Design of siLNA in Mammalian Reporter System

The efficacy of different siLNA designs and combinations were first assessed in a luciferase reported system in mammalian cell culture. The oligonucleotides used are shown in Table 1. Sense and the corresponding antisense oligonucleotides were hybridised to generate double strands, i.e. siRNA or siLNA.

The cells used were the human embryonal kidney (HEK) 293 cell lines. HEK 293 cells were maintained in DMEM supplemented with 10% foetal bovine serum, penicillin, streptomycine and glutamine (Invitrogen, Paisely, UK). The plasmids used were pGL3-Control coding for firefly luciferace under the control of the SV40 promoter and enhancer and pRL-TK coding for *Renilla* luciferase under the control of HSV-TK promoter (Promega, Madison, Wis., USA).

Transfection

One day before transfection cells were seeded in 500 µl medium in 24-well plates in order to adhere and reach a confluency of 70 to 90% at the time of transfection. Cells were seeded in the medium without antibiotics and changed to 500 µl Opti-MEM I just before adding the transfection mix to the cells. A standard co-transfection mix was prepared for triplicate wells by separately adding 510 ng pGL3-Control, 51 ng pRL-TK and 340 ng siRNA to 150 µl Opti-MEM I (Invitrogen) and 3 µl LipofectAMINE 2000 (Invitrogen) to another 150 µl Opti-MEM I. The two solutions were mixed and incubated at room temperature for 20-30 minutes before adding to the cells. 100 µl of the transfection mix was added to each of the three wells. The final volume of medium plus transfection mix was 600 µl. The siLNA or siRNA concentration corresponded to about 13 nM. Cells were incubated with the transfection mix for 4 hours and the medium was then changed with fully supplemented DMEM.

Dual-Luciferase Reporter Assay (Promega)

Cells were harvested in passive lysis buffer and assayed according to the protocol (Promega) using a NovoSTAR 96-well format luminometer with substrate dispenser (BMG Labtechnologies, Offenburg, Germany). 10 µl sample was applied in each well of a 96 well plate and 50 µl Luciferace Assay Reagent II (substrate for firefly luciferase) was added to a well by the luminometer and measured. Then, 50 µl Stop and Glow (stop solution for firefly luciferase and substrate for *Renilla* luciferase) was added and measured. The average of the luciferase activities measured for 10 sec. was used to calculate ratios between firefly and *Renilla* luciferase or the opposite.

Example 6

In Vitro Model: Assessment Off Efficacy on an Endogenous Target

Figure 3:
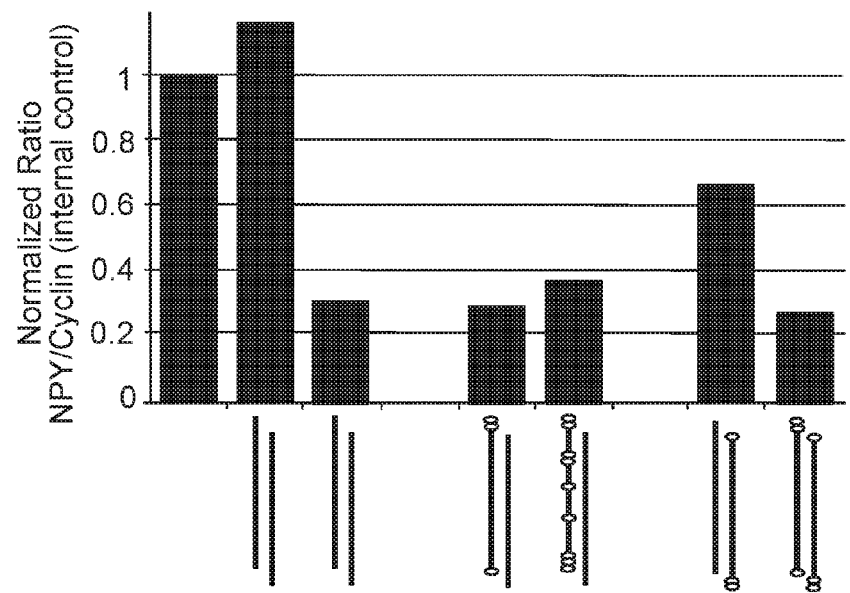
FIG. 3 shows the down-regulation of the endogenous NPY gene in PC12 cells by siLNAs. The tested compounds were (from left to right): 2nd bar: unrelated siRNA; 3rd bar: NPY+/1, 4th bar: 2796/NPY−; 5th bar: 2795/NPY+; 6th bar: NPY+/2797; 7th bar: 2796/2797.

The cells used were the rat adrenal pheochromocytoma, PC12 cell lines. PC12 were maintained in DMEM supplemented with 10% horse serum, 5% foetal bovine serum, penicillin, streptomycine and glutamine. The SiLNA or siRNA transfection protocol for endogenous genes (like NPY in PC12 cells) follows the same procedure as described above but without luciferase plasmids and only adding siRNA targeting NPY (since the NPY gene is endogenously expressed in PC12 cells). Final siLNA or siRNA concentrations ranged from 1 to 100 nM. Cells were usually harvested 24 to 48 hours post transfection and mRNA was extracted. mRNA levels were measured with Real-Time PCR. The down-regulation of the NPY target in PC12 is shown in FIG. 3, Example 7

In Vitro Model: Analysis of Inhibition of Target

Expression by Real-Time PCR

SiLNA or siRNA gene silencing of a target can be assayed in a variety of ways known in the art. For example, target mRNA levels can be quantified by, e.g., Northern blot analysis, competitive polymetargete chain reaction (PCR), or real-time PCR. Real-time quantitative PCR is presently preferred.

RNA analysis can be performed on total cellular RNA or mRNA. Methods of RNA isolation and RNA analysis, such as Northern blot analysis, is routine in the art and is taught in, for example, Current Protocols in Molecular Biology, John Wiley and Sons.

Cells were harvested and mRNA was extracted. Standard real-time PCR protocols were used to amplify target genes from mRNA with gene specific primers along with a primer pair towards a housekeeping gene as internal control (such as Cyclophilin). Down-regulation was expressed as a ratio of amount target mRNA to amount control mRNA. Real-time quantitative (PCR) can be conveniently accomplished using the commercially available iQ Multi-Color Real Time PCR Detection System, available from BioRAD.

Example 8

Figure 4:
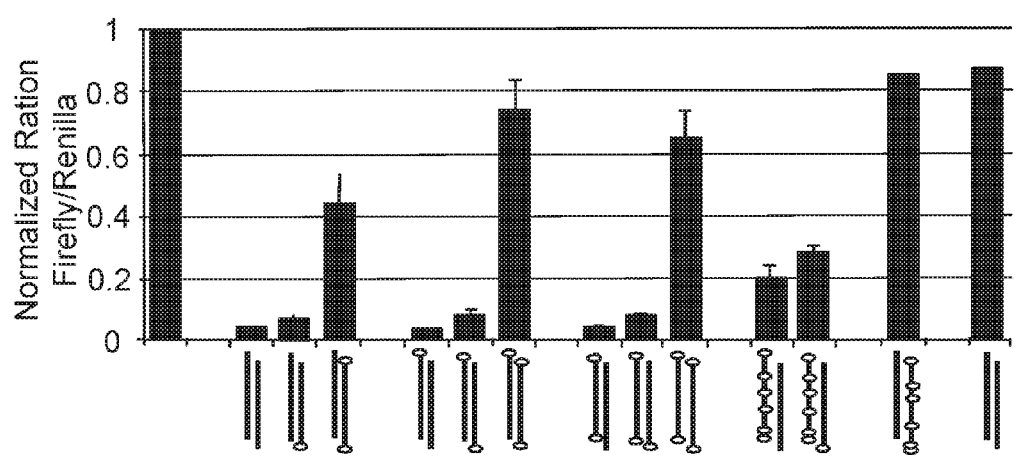
FIG. 4 shows the effect of siLNA in targeting firefly luciferase and modulation of the expression. The left lines represent the sense strand and the right lines represent the antisense strand of the siLNA. The marks on the individual lines represent the position of the LNA monomers. The last two lines on the right represent control siRNA. The first bar (on the left) represents full, non-modulated, luciferase reporter expression to which all samples are normalised. The tested compounds were (from left to right): 2nd bar: GL3+/−; 3rd bar: GL3+/2186; 4th bar: GL3+/2187; 5th bar: 2184/GL3−; 6th bar: 2184/2186; 7th bar: 2184/2187; 8th bar: 2185/GL3−; 9th bar: 2185/2186; 10th bar: 2185/2187; 11th bar: 2703-1/GL3−; 12th bar: 2703-1/2186; 13th bar: GL3+/2189; 14th bar: unrelated siRNA.
Figure 5:
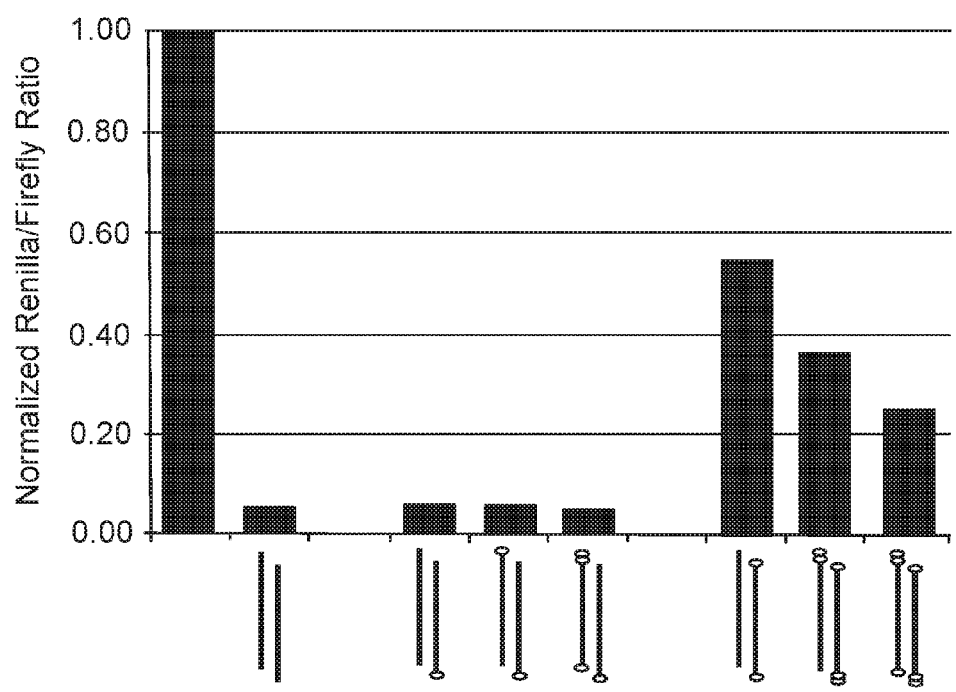
FIG. 5 shows the effect of siLNA in targeting Renilla luciferase and modulation of the expression. The left lines represent the sense strand and the right lines represent the antisense strand of the siLNA. The marks on the individual lines represent the position of the LNA monomers. The first bar represents full, non-modulated luciferase reporter expression, to which all samples are normalised. The tested compounds were (from left to right): 2nd bar: RL+/−; 3rd bar: RL+/2699-1; 4th bar: 2700-1/2699-1; 5th bar: 2702-1/2699-1; 6th bar: RL+/2701-1; 7th bar: 2700-1/2701-1; 8th bar: 2702-1/2701-1.
Figure 6:
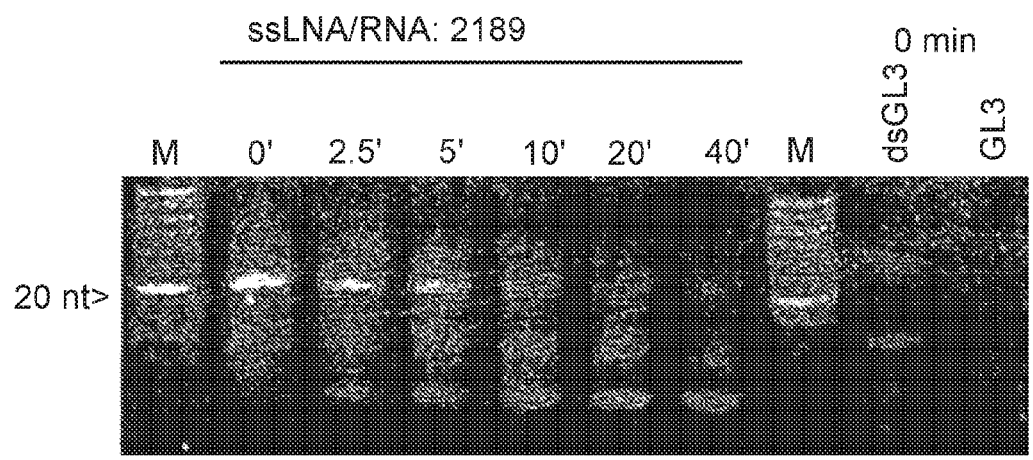
FIG. 6 shows the stability in rat serum of single-stranded oligos containing LNA and RNA monomers, double-stranded (ds) RNA and single-stranded (ss) RNA. dsRNA and ssRNA were degraded immediately while intact single-stranded oligos containing LNA and RNA monomers could be detected after 20-40 minutes. The tested oligos were 2189 and the corresponding ssRNA (GL3−) and dsRNA (GL3+/1).

In Vitro Analysis: SiRNA Inhibition of Reporter Target Expression siLNA Oligonucleotides LNA monomers could be used to modify both ends of the sense strand in siRNA with a maintained effect as compared to siRNA (>90% inhibition of Firefly Luciferase expression compared to untreated samples). The antisense strand could also be modified in the 3' end without loss of efficiency while a modification in the 5' end of the antisense strand reduced the effect to 25-50% inhibition. By exchanging all uracil-containing residues to LNA thymines in the sense strand reduced the effect to 80% inhibition. A similar modification of the antisense strand abolished the effect (FIG. 4). Phosphorylation of the 5' end of the siLNA antisense strand did not improve the reduction (20-30% reduction, data not shown). Similar experiments targeting *Renilla* Luciferase showed that both ends of the sense strand could be modified with LNA monomers while the antisense strand tolerates 3' end LNA monomer modification (95% inhibition in all cases), but showed less inhibition with both a 3' and a 5' end LNA modification. Still up to 75% inhibition was observed (FIG. 5). Stability of LNA/RNA was measured on all RNA uracil to LNA thymidine oligo (2189) in 100% rat serum, where the stability was similar to naked DNA oligos. An unmodified RNA single strand (GL3−) and unmodified double strand (GL3+/−) were degraded already at time point zero (FIG. 6).

Example 9

In Vitro Analysis: siRNA Inhibition of Endogenious Target by siLNA

Inhibition of Cytotoxicity

Figure 8:
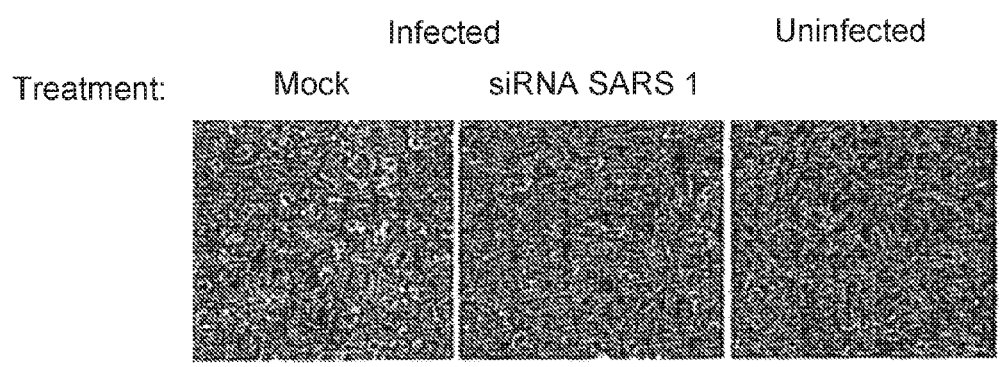
FIG. 8 shows the cytopathic effect (CPE) in vero cells when infected with SARS and the reduced CPE after siRNA treatment. Shown is siRNA SARS 1. Mock is treated with the transfection agent lipofectamine 2000 alone. Also shown is non-infected cells.
Figure 9:
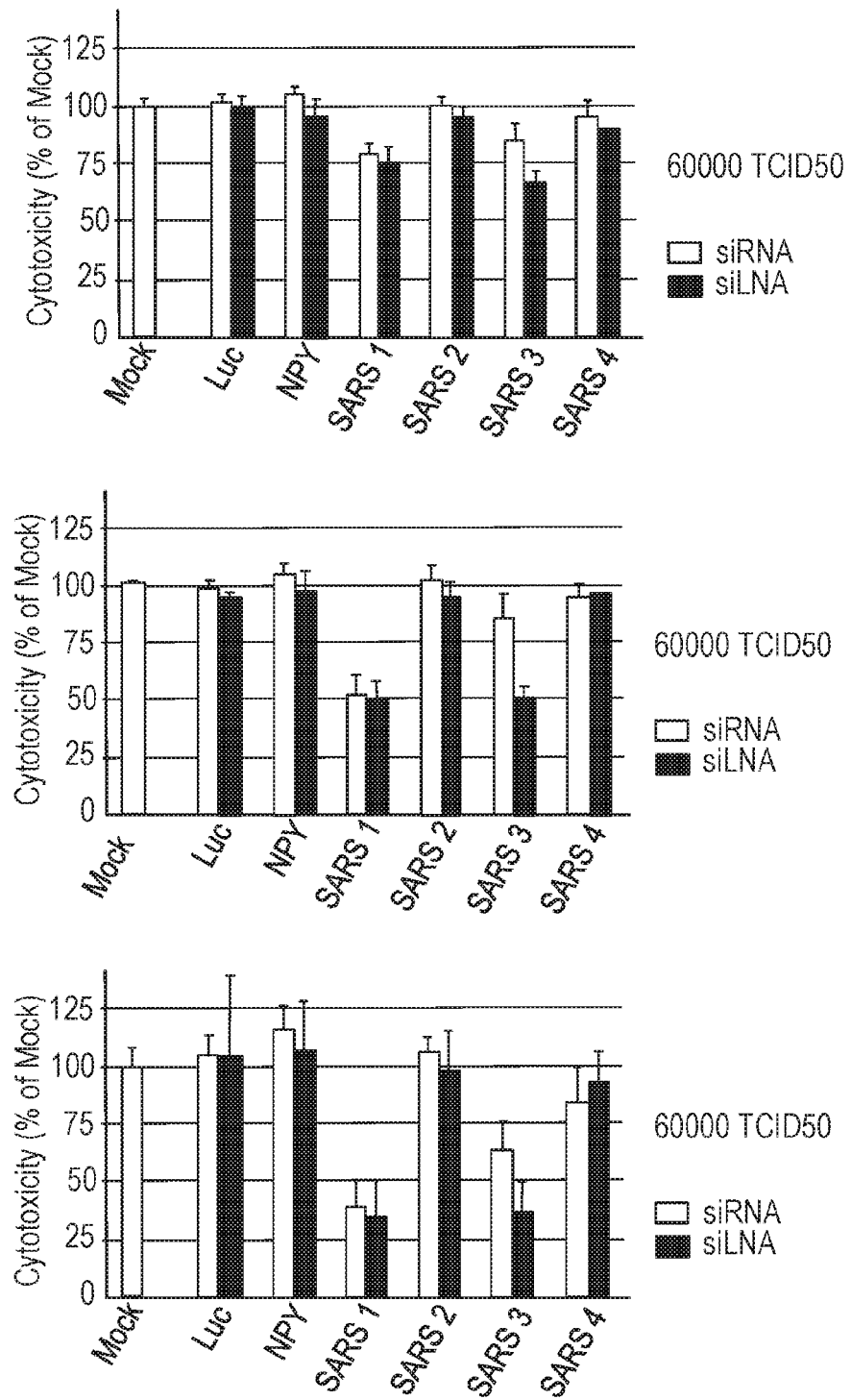
FIG. 9 shows inhibition of SARS-induced cytotoxicity by siRNA and siLNA. The tested compounds were: SARS 1: 2842-1/2843-1; SARS 2872-1/2845-1; SARS 3: 2846-1/2847-1; SARS 4: 2848-1/2849-1 as well as the corresponding unmodified siRNAs. No difference in the treatment with siLNA and siRNA could be detected for the most efficient site, SARS 1. The medium efficient site, SARS 3, was improved by siLNA to be as efficient as the SARS 1 site. The two sites that did not shown siRNA efficiency at all, SARS 2 and SARS 4, did not show any effect by siLNA treatment either. The inhibitory effect is reduced at high viral doses (60,000 TCID50). Controls were luciferase (Luc) and neuropeptide Y (NPY) siRNA and siLNA. No adverse effects were seen by the siLNA controls. Cytotoxicity was measured as lactate dehydrogenase (LDH) release at 50 hours post infection. The different graphs represent different viral doses (tissue culture infectious dose 50, TCID50).

Cells were transfected with 85 nM of the respective siRNA or siLNA (SARS 1-4, see FIG. 7) or with control siRNA targeting the firefly luciferase gene (Luc) or the rat neuropeptide Y (NPY) gene. Mock-transfected cells were treated with Lipofectamine 2000 only and used as positive control. Uninfected cells were included as negative control. Transfected cells were infected with either 60,000, 6,000 or 600 $TCID_{50}$ of SARS-CoV. After 50 hours of infection, the CPE and the cytotoxicity was measured. There was a marked difference in CPE between the cells treated with the most effective siRNA, SARS 1, as compared to mock-transfected cells (FIG. 8). The cytotoxicity was determined as percent LDH release from treated cells as compared to mock-transfected control cells. The percent inhibition of cytotoxicity was calculated as 100−percent cytotoxicity in the siRNA treated sample. The four Pol-specific siRNA and siLNA had various effects on cytotoxicity (FIG. 9). The most effective siRNA and siLNA were the ones targeting the SARS 1 site, which reduced cytotoxicity and with up to 65% at 600 $TCID_{50}$. The SARS 3 site was medium efficient using siRNA at all three viral doses. However SARS 3 became an equally efficient site as SARS 1 by using siLNA, also at all three viral doses. The sites SARS 2 and SARS 4 did no show any effect by siRNA or siLNA at any viral dose. The data represent mean and standard deviation determined by three independent experiments in quadruplicate.

Virus and Cells

Vero cells were used for all cellular experiments. Cells were cultivated in phenol red-free Eagle's MEM containing 5% FCS and 1% PEST at 37° C. and 5% $CO_2$. The Frankfurt 1 isolate (GenBank accession number AY291315, kindly provided by Dr. H. W. Doerr) was grown to high titers on Vero cells. Supernatants from two T225 cell culture flasks were pooled and frozen at −80° C. in 1 ml vials and constituted the viral stock. The stock virus was identified as SARS-CoV by diagnostic reverse transcriptase PCR using the BNIoutS2 and BNIoutAs[11] primers and the Cor-p-F2 and Cor-p-R1 primers[2]. The virus stock was used in ten-fold dilutions or at a fixed dilution to infect Vero cells in 96 well cell culture plates. The virus stock was diluted 600,000 times (determined by the Reed-Muench method) to reach $TCID_{50}$ in 96 well cell culture plates.

The siLNA oligonucleotides were produced as described above. The sequence are shown in FIG. 7.

Tranfections

Lipofectamine-2000 (Invitrogen) was used to transefect the cells with siRNA and siLNA. Transfection efficiency was high and most cell were transfected. The transfection medium was changed to phenol red-free Eagle's MEM after four hours, and cells were grown overnight to form a confluent monolayer.

Cytopathogenicity and Cytotoxicity

The cytopathogenic effect (CPE) on infected cells was detected as cell rounding and detachment from the cell culture plate. The CPE was scored in a light microscope. The cytotoxicity was measured using a cytotoxicity detection kit (LDH) (Roche, Germany). Mock-transfected cells treated with lipofectamine-2000 only were set as 100% cytotoxicity caused by the virus infection at each viral dilution. Uninfected cells were used to determine the background cytotoxicity. The percent cytotoxicity was determined as [((Abs490 sample−background)/(Abs490 mock-transfected controls−background))×100]. The inhibition of cytotoxicity was calculated as [(1−(Abs490 sample−background)/(Abs490 mock-transfected controls−background))×100].

Example 10

Reduction of Off-Site Effects

Inhibition of SARS sense/antisense target in 3'UTR of firefly luciferase was performed at 1.6 nM siRNA/siLNA with the plasmids: pS3Xs (pGL3 with SARS sense target), pS3Xas (pGL3 with SARS antisense target), and pGL3 (without SARS target).

The SARS 3 target sequence was cloned in sense (sequence corresponding to the SARS mRNA) and antisense direction (complementary sequence to the SARS mRNA) in firefly luciferase 3' UTR, between the luciferase coding region and poly A in pGL3. pGL3 was cut with Xba I (between luc. stop codon and poly A) and a SARS 53 target sequence DNA oligo duplex with Xba I overhangs.

(SARS 3 target (SARS genomic position 14593) DNA oligo duplex with Xba I overhangs) 5'- ctagcaaactgtcaaacccggtaattttc-3' (sense, same as mRNA) 3'-gtttgacagtttgggccattaaaaagatc-5' (antisense, complementary to the mRNA)

Ligation of the oligo duplex resulted in two plasmid products with either sense or antisense target (pS3Xs: target in sense direction, pS3Xas: target in antisense direction). The two different plasmids were transfected into separate HEK293 cell cultures along with control plasmid pRL-TK and siRNA targeting SARS3 or siLNA targeting SARS3 (final concentration 1.6 nM), according to protocol described in Example 5. Cells were incubated for 24 hours, cells were harvested and luciferase activity measured as described in Example 5.

siLNA can inactivate the unwanted sense strand while maintaining full effect of the antisense strand. siRNA shows effect of both strands. SARS 3 target sequence was cloned in both sense and antisense direction where after siLNA and siRNA where assayed for inhibitory effects on two the different plasmids.

siRNA shows down-regulation of both sense target (part from SARS mRNA sequence, ~90% reduction of luciferase activity) as well as the antisense target (complementary sequence to the SARS mRNA) (~50% reduction). Hence both the sense and antisense strand in the siRNA have a down regulatory effect. However, siLNA SARS 3 shows equally good effect down-regulating the sense target (~90% reduction) while there is no activity on the antisense target (0% reduction). Hence the antisense strand in the siLNA maintains full effect while the effect of the unwanted sense strand is abolished. This means that siLNA can minimize off-targets by the sense strand by inactivating it to the RNA interference machinery (FIG. 17).

Example 11

In Vivo Efficacy of siLNA

The purpose of this study was to test the in vivo efficacy of two anti eGFP siRNAs which have been modified by incorporation of LNA monomers. The used compounds were 3029/3031 and 3030/3031.

In brief, female nude mice (NMRI nu/nu, Charles River Netherlands, Maastricht, The Netherlands) were injected with 15PC3 and Miapaca xenografts. The 15PC3 cells and Miapaca cells express eGFP as described by Fluiter et al. (2002) Cancer Research 62, 2024-2028.

After two weeks of tumor growth the mice were subcutaneously fitted with Osmotic minipumps (Alzet 1007D, lot no. 10052-02 (7 day pumps) (Durect Corporation, Cupertino, Calif.)). These pumps were filled with either 3029/3031 or 3030/3031 to give a dosage of 0.5 mg/kg/day. The mic were treated for 5 days. At the 5th day the mice were sacrificed and the tumor fluorescence was imaged and measured using a LAS3000 luminesent image analyser (Fujifilm). The fluorescence was quantified using AIDA software (Raytest GmbH, Straubenhardt, Germany). After imaging the tumors were taken out and stored for protein analysis (western blot). The obtained results for 15PC3 are shown in FIG. 18. As can be seen the siLNA compounds had a significant effect on tumor growth. Similar results were obtained with the Miapaca xenograft model.

The siLNA was checked prior to implantation and after the experiment (leftover in the pump) using MALDI-tof analysis. The siLNA was purified by ion exchange on the purification plates from the Nucleave genotyping kit (Waters, Milford, Mass., USA) and analyzed using Matrix-assisted laser desorption ionization time-of-flight mass spectrometry (MALDI-TOF) on a Biflex III MALDI (Brucker Instruments, Leipzig, Germany). Data are shown in FIG. 20.

TABLE 1

| No | Sequence (5'→3') | Conc. (μM) | Purity |
|---|---|---|---|
| 2184 | cuuacgcugaguacuucgaTT | 440 | ~80% |
| 2185 | $^{Me}$Cuuacgcugaguacuucga TT | 320 | ~70% |
| 2186 | ucgaaguacucagcguaagTT | 380 | ~65% |
| 2187 | TcgaaguacucagcguaagTT | 340 | ~60% |
| 2187-phos | Phos-TcgaaguacucagcguaagTT | 350 | ~80% |
| 2188 | $^{Me}$CTTcgcTagTacTTcgaTT | 410 | ~50% |
| 2189 | TcgaagTacTcagcgTaagTT | 390 | ~55% |
| 2189-phos | Phos-TcgaagTacTcagcgTaagTT | 330 | ~80% |
| 2699-1 | uuuuucuccuucuucagauTT | 400 | ~80% |
| 2700-1 | aucugaagaaggagaaaaaTT | 400 | ~80% |
| 2701-1 | TuuuucuccuucuucagauTT | 360 | ~80% |
| 2702-1 | AucugaagaaggagaaaaaTT | 430 | ~80% |
| 2703-1 | $^{Me}$CTTacgcTgagTacTTcgaTT | 500 | ~80% |

Capital letters: Beta-D-oxy LNA monomer
Small letters: RNA monomer
Phos: 5'-phosphate
$^{Me}$C: 5-methylcytosine

TABLE 2

| No | Sequence (5'→3') |
|---|---|
| 2780 | $^{Me}$CTTA$^{Me}$CG$^{Me}$CTGAGTA$^{Me}$CTT$^{Me}$CGATT |
| 2781 | $_{d}$cT$_{d}$tA$_{d}$cG$_{d}$cT$_{d}$gA$_{d}$gT$_{d}$a$^{Me}$C$_{d}$tT$_{d}$cG$_{d}$aTT |
| 2782 | $_{d}$cT$_{d}$t$_{d}$a$^{Me}$C$_{d}$g$_{d}$cT$_{d}$g$_{d}$aG$_{d}$t$_{d}$a$^{Me}$C$_{d}$t$_{d}$t$^{Me}$C$_{d}$g$_{d}$aTT |
| 2783 | $^{Me}$CuuAcGcuGaGua$^{Me}$Cuu$^{Me}$CgaTT |
| 2784 | $^{Me}$C$_{d}$u$_{d}$uA$_{d}$cG$_{d}$c$_{d}$uG$_{d}$aG$_{d}$u$_{d}$a$^{Me}$Cu$_{d}$u$^{Me}$C$_{d}$g$_{d}$aTT |
| 2785 | u$^{Me}$CGAAGTA$^{Me}$CT$^{Me}$CAG$^{Me}$CGTAAGTT |
| 2786 | u$^{Me}$C$_{d}$gA$_{d}$aG$_{d}$tA$_{d}$cT$_{d}$cA$_{d}$g$^{Me}$C$_{d}$gT$_{d}$aA$_{d}$gTT |
| 2787 | u$^{Me}$C$_{d}$g$_{d}$aA$_{d}$g$_{d}$tA$_{d}$c$_{d}$t$^{Me}$C$_{d}$a$_{d}$g$^{Me}$C$_{d}$g$_{d}$tA$_{d}$a$_{d}$gTT |
| 2788 | ucGaaGua$^{Me}$CucAgcGuAagTT |
| 2789 | u$^{Me}$CgaaguacucagcguaagTT |
| 2790 | ucGaaguacucagcguaagTT |
| 2792 | ucgaAguacucagcguaagTT |
| 2793 | ucgaaGuacucagcguaagTT |
| 2794 | ucgaaguAcucagcguaagTT |
| 2795 | TgAgAgaaAgcAcAgaAaaTT |

TABLE 2-continued

| No | Sequence (5'→3') |
|---|---|
| 2796 | TgagagaaagcacagaaaaTT |
| 2797 | TuuucugugcuuucucucaTT |

Capital letters: Beta-D-oxy LNA monomer
Small letters without prefix: RNA monomer
Small letters with "d" prefix: DNA monomer
$^{Me}$C: 5-methylcytosine

TABLE 3

| No | Sequence (5'→3') |
|---|---|
| 2842-1 | GgaugaggaaggcaauuuaTT |
| 2843-1 | uaaauugccuuccucauccTT |
| 2872-1 | CugguacgauuucggugauTT |
| 2845-1 | aucaccgaaaucguaccagTT |
| 2846-1 | AcugucaaacccgguaauuTT |
| 2847-1 | aauuaccggguuugacaguTT |
| 2848-1 | GacaacuccuauucguaguTT |
| 2849-1 | acuacgaauaggaguugucTT |
| 2862-1 | UccagaacaaaccaaacggTT |
| 2863-1 | AaacaugcagaaaaugcugTT |
| 2864-1 | ucgaagua$^{Me}$CucagcguaagTT |
| 2865-1 | ucgaaguacTcagcguaagTT |
| 2866-1 | ucgaaguacu$^{Me}$CagcguaagTT |
| 2867-1 | ucgaaguacucAgcguaagTT |
| 2865-U | ucgaaguacAcagcguaagTT |
| 3029 | GcugacccugaaguucaucTT |
| 3030 | G$^{Me}$CTgac$^{Me}$CcuGaagTTcaucTT |
| 3031 | gaugaacuucagggucagcTT |

Capital letters: Beta-D-oxy LNA monomer
Small letters without prefix: RNA monomer
$^{Me}$C: 5-methylcytosine

The invention claimed is:

1. A double-stranded compound comprising a sense strand and an antisense strand, wherein each strand comprises 12-35 nucleotides, wherein at least one of the strands has a 3' overhang and wherein said compound comprises at least one locked nucleic acid (LNA) monomer located at the 5' end of the sense strand.

2. The compound according to claim 1, wherein at least three LNA monomers are located at the 3' end of the antisense strand.

3. The compound according to claim 1, wherein no LNA monomer is located at the 5' end of the antisense strand.

4. The compound according to claim 1, wherein the sense strand comprises 1-10 LNA monomers and the antisense strand comprises 1-10 LNA monomers.

5. The compound according to claim 1, wherein the sense strand comprises at least one LNA monomer at the 5' end and at least one LNA monomer at the 3' end, and wherein the antisense strand comprises at least one LNA monomer at the 3' end.

6. The compound according to claim 1, wherein the sense strand comprises at least one LNA monomer at the 5' end and at least one LNA monomer at the 3' end, and wherein the antisense strand comprises at least two LNA monomers at the 3' end.

7. The compound according to claim 1, wherein the sense strand comprises at least two LNA monomers at the 5' end and at least two LNA monomers at the 3' end, and wherein the antisense strand comprises at least two LNA monomers at the 3' end.

8. The compound according to claim 1, wherein the sense strand comprises at least two LNA monomers at the 5' end and at least two LNA monomers at the 3' end, and wherein the antisense strand comprises at least three LNA monomers at the 3' end.

9. The compound according to claim 4, wherein no LNA monomer is located at the 5' end of the antisense strand.

10. The compound according to claim 1, wherein the sense strand comprises at least one LNA monomer in at least one of positions 9-13 counted from the 5' end.

11. The compound according to claim 1, wherein the sense strand comprises a LNA monomer in position 10.

12. The compound according to claim 1, wherein the sense strand comprises a LNA monomer in position 11.

13. The compound according to claim 1, wherein the sense strand comprises a LNA monomer in position 12.

14. The compound according to claim 1, wherein each strand comprises 20-22 nucleotides.

15. The compound according to claim 1, wherein the LNA monomer is in the beta-D form.

16. A pharmaceutical composition comprising the compound according to claim 1 and a pharmaceutically acceptable diluent, carrier or adjuvant.

17. The compound according to claim 1 wherein the nucleobase of the LNA monomer at position 10 is thymine (T).

18. The compound according to claim 1 wherein at least one 3' overhang is 1-3 nucleotides in length.

19. The compound according to claim 1 wherein the at least one 3' overhang is 1-3 nucleotides in length, and wherein there is no LNA monomer located at the 5' end of the antisense strand.

20. The compound according to claim 1 wherein the at least one 3' overhang is 1-3 nucleotides in length, wherein there is no LNA monomer located at the 5' end of the antisense strand, and wherein there is at least one LNA monomer at the 5' end of the sense strand.

21. The compound according to claim 1, wherein both the sense strand and the antisense strand comprise a 3' overhang.

22. The compound according to claim 1, wherein both the sense strand and the antisense strand comprise a 3' overhang and wherein each 3' overhang is, independently, 1-3 nucleotides in length.

23. The compound according to claim 1, wherein both the sense strand and the antisense strand comprise a 3' overhang, and wherein each 3' overhang is 3 nucleotides in length.

24. The compound according to claim 1, wherein both the sense strand and the antisense strand comprise a 3' overhang, wherein each 3' overhang is, independently, 1-3 nucleotides in length, and wherein there is no LNA monomer located at the 5' end of the antisense strand.

25. The compound according to claim 1, wherein both the sense and antisense strand comprise a 3' overhang, wherein each 3' overhang is, independently, 1-3 nucleotides in length, wherein there is no LNA monomer located at the 5' end of the antisense strand, and wherein there is at least one LNA monomer at the 5' end of the sense strand.

26. The compound according to claim 1, wherein both the sense strand and the antisense strand comprise a 3' overhang, wherein each 3' overhand is, independently, 1-3 nucleotides in length, wherein there is no LNA monomer located at the 5' end of the antisense strand, and wherein at least two LNA monomers are located at the 3' end of the antisense strand.

27. The compound according to claim 1, wherein both the sense strand and antisense strand comprise a 3' overhang, wherein each 3' overhang is, independently, 1-3 nucleotides in length, and wherein there is no LNA monomer located at the 5' end of the antisense strand, wherein the antisense strand comprises at least one LNA monomer at the 3' end, and wherein the sense strand comprises at least one LNA monomer at the 5' end and at least one LNA monomer at the 3' end.

28. The compound according to claim 1, wherein both the sense strand and the antisense strand comprise a 3' overhang, wherein each 3' overhang is, independently, 1-3 nucleotides in length, wherein there is no LNA monomer located at the 5' end of the antisense strand, wherein the antisense strand comprises at least one LNA monomer at the 3' end, wherein the sense strand comprises at least one LNA monomer at the 5' end and at least one LNA monomer at the 3' end, and wherein the sense strand comprises at least one LNA monomer in at least one of positions 9-13 counted from the 5' end.

29. The compound according to claim 1, wherein both the sense and antisense strand comprise a 3' overhang, wherein each 3' overhang is, independently, 3 nucleotides in length, wherein there is no LNA monomer located at the 5' end of the antisense strand, wherein the antisense strand comprises at least one LNA monomer at the 3' end, wherein the sense strand comprises at least one LNA monomer at the 5' end and at least one LNA monomer at the 3' end.

30. The compound according to claim 1, wherein both the sense and antisense strand comprise a 3' overhang, wherein each 3' overhang is, independently, 3 nucleotides in length, wherein there is no LNA monomer located at the 5' end of the antisense strand, wherein the antisense strand comprises at least one LNA monomer at the 3' end, wherein the sense strand comprises at least one LNA monomer at the 5' end and at least one LNA monomer at the 3' end, and wherein the sense strand comprises at least one LNA monomer at least one of positions 9-13 counted from the 5' end.

* * * * *

SEQUENCE LISTING

<160> NUMBER OF SEQ ID NOS: 62

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 1
cuuacgcuga guacuucgat                                                  20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 5-methylcytosine/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 2
cuuacgcuga guacuucgat t                                                21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 3
ucgaaguacu cagcguaagt t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 4
tcgaaguacu cagcguaagt t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: phosphate-t/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 5
tcgaaguacu cagcguaagt t                                              21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

```
          Synthetic oligonucleotide
<220> FEATURE:
<221> NAME/KEY: modified_base
<222> LOCATION: (1)..(1)
<223> OTHER INFORMATION: 5-methylcytosine/Beta-D-oxy LNA monomer
<220> FEATURE:
<221> NAME/KEY: modified_base
<222> LOCATION: (2)..(3)
<223> OTHER INFORMATION: Beta-D-oxy LNA monomer
<220> FEATURE:
<221> NAME/KEY: modified_base
<222> LOCATION: (7)..(7)
<223> OTHER INFORMATION: Beta-D-oxy LNA monomer
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (13)..(14)
<223> OTHER INFORMATION: Beta-D-oxy LNA monomer
<220> FEATURE:
<221> NAME/KEY: modified_base
<222> LOCATION: (18)..(19)
<223> OTHER INFORMATION: Beta-D-oxy LNA monomer

<400> SEQUENCE: 6
cttcgctagt acttcgatt                                                    19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (7)..(7)
<223> OTHER INFORMATION: Beta-D-oxy LNA monomer
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (16)..(16)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 7
tcgaagtact cagcgtaagt t                                                 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (1)..(1)
<223> OTHER INFORMATION: phosphate-t/Beta-D-oxy LNA monomer
<220> FEATURE:
<221> NAME/KEY: modified_base
<222> LOCATION: (7)..(7)
<223> OTHER INFORMATION: Beta-D-oxy LNA monomer
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (16)..(16)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 8
tcgaagtact cagcgtaagt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 9
uuuucucccu ucuucagaut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 10
aucugaagaa ggagaaaaat t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
```

```
<221> NAME/KEY: modified_base
<222> LOCATION: (20)..(21)
<223> OTHER INFORMATION: Beta-D-oxy LNA monomer

<400> SEQUENCE: 11
tuuuucuccu ucuucagaut t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 12
aucugaagaa ggagaaaaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 5-methylcytosine/Beta-D-oxy LNA monomer
<220> FEATURE:
<221> NAME/KEY: modified_base
<222> LOCATION: (2)..(3)
<223> OTHER INFORMATION: Beta-D-oxy LNA monomer
<220> FEATURE:
<221> NAME/KEY: modified_base
<222> LOCATION: (8)..(8)
<223> OTHER INFORMATION: Beta-D-oxy LNA monomer
<220> FEATURE:
<221> NAME/KEY: modified_base
<222> LOCATION: (12)..(12)
<223> OTHER INFORMATION: Beta-D-oxy LNA monomer
<220> FEATURE:
<221> NAME/KEY: modified_base
<222> LOCATION: (15)..(16)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 13
cttacgctga gtacttcgat t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 5-methylcytosine
<220> FEATURE:
<221> NAME/KEY: modified_base
<222> LOCATION: (5)..(5)
<223> OTHER INFORMATION: 5-methylcytosine
<220> FEATURE:
<221> NAME/KEY: modified_base
<222> LOCATION: (7)..(7)
<223> OTHER INFORMATION: 5-methylcytosine
<220> FEATURE:
<221> NAME/KEY: modified_base
<222> LOCATION: (14)..(14)
<223> OTHER INFORMATION: 5-methylcytosine
<220> FEATURE:
<221> NAME/KEY: modified_base
<222> LOCATION: (17)..(17)
<223> OTHER INFORMATION: 5-methylcytosine
<220> FEATURE:
<221> NAME/KEY: modified_base
<222> LOCATION: (1)..(21)
<223> OTHER INFORMATION: Beta-D-oxy LNA monomer

<400> SEQUENCE: 14
cttacgctga gtacttcgat t                                           21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: Beta-D-oxy LNA monomer
<220> FEATURE:
<221> NAME/KEY: modified_base
<222> LOCATION: (4)..(4)
<223> OTHER INFORMATION: Beta-D-oxy LNA monomer
<220> FEATURE:
<221> NAME/KEY: modified_base
<222> LOCATION: (6)..(6)
<223> OTHER INFORMATION: Beta-D-oxy LNA monomer
<220> FEATURE:
<221> NAME/KEY: modified_base
<222> LOCATION: (8)..(8)
<223> OTHER INFORMATION: Beta-D-oxy LNA monomer
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (12)..(12)
<223> OTHER INFORMATION: Beta-D-oxy LNA monomer
<220> FEATURE:
<221> NAME/KEY: modified_base
<222> LOCATION: (14)..(14)
<223> OTHER INFORMATION: 5-methylcytosine/Beta-D-oxy LNA monomer
<220> FEATURE:
<221> NAME/KEY: modified_base
<222> LOCATION: (16)..(16)
<223> OTHER INFORMATION: Beta-D-oxy LNA monomer
<220> FEATURE:
<221> NAME/KEY: modified_base
<222> LOCATION: (18)..(18)
```

<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 15
cttacgctga gtacttcgat t                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: Beta-D-oxy LNA monomer
<220> FEATURE:
<221> NAME/KEY: modified_base
<222> LOCATION: (5)..(5)
<223> OTHER INFORMATION: 5-methylcytosine/Beta-D-oxy LNA monomer
<220> FEATURE:
<221> NAME/KEY: modified_base
<222> LOCATION: (8)..(8)
<223> OTHER INFORMATION: Beta-D-oxy LNA monomer
<220> FEATURE:
<221> NAME/KEY: modified_base
<222> LOCATION: (11)..(11)
<223> OTHER INFORMATION: Beta-D-oxy LNA monomer
<220> FEATURE:
<221> NAME/KEY: modified_base
<222> LOCATION: (14)..(14)
<223> OTHER INFORMATION: 5-methylcytosine/Beta-D-oxy LNA monomer
<220> FEATURE:
<221> NAME/KEY: modified_base
<222> LOCATION: (17)..(17)
<223> OTHER INFORMATION: 5-methylcytosine/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 16
cttacgctga gtacttcgat t                                          21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 5-methylcytosine/Beta-D-oxy LNA monomer
<220> FEATURE:
<221> NAME/KEY: modified_base
<222> LOCATION: (4)..(4)
<223> OTHER INFORMATION: Beta-D-oxy LNA monomer
<220> FEATURE:
<221> NAME/KEY: modified_base
<222> LOCATION: (6)..(6)
<223> OTHER INFORMATION: Beta-D-oxy LNA monomer
<220> FEATURE:
<221> NAME/KEY: modified_base

```
<222> LOCATION: (9)..(9)
<223> OTHER INFORMATION: Beta-D-oxy LNA monomer
<220> FEATURE:
<221> NAME/KEY: modified_base
<222> LOCATION: (11)..(11)
<223> OTHER INFORMATION: Beta-D-oxy LNA monomer
<220> FEATURE:
<221> NAME/KEY: modified_base
<222> LOCATION: (14)..(14)
<223> OTHER INFORMATION: 5-methylcytosine/Beta-D-oxy LNA monomer
<220> FEATURE:
<221> NAME/KEY: modified_base
<222> LOCATION: (17)..(17)
<223> OTHER INFORMATION: 5-methylcytosine/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 17
cuuacgcuga guacuucgat t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 5-methylcytosine/Beta-D-oxy LNA monomer
<220> FEATURE:
<221> NAME/KEY: modified_base
<222> LOCATION: (4)..(4)
<223> OTHER INFORMATION: Beta-D-oxy LNA monomer
<220> FEATURE:
<221> NAME/KEY: modified_base
<222> LOCATION: (6)..(6)
<223> OTHER INFORMATION: Beta-D-oxy LNA monomer
<220> FEATURE:
<221> NAME/KEY: modified_base
<222> LOCATION: (9)..(9)
<223> OTHER INFORMATION: Beta-D-oxy LNA monomer
<220> FEATURE:
<221> NAME/KEY: modified_base
<222> LOCATION: (11)..(11)
<223> OTHER INFORMATION: Beta-D-oxy LNA monomer
<220> FEATURE:
<221> NAME/KEY: modified_base
<222> LOCATION: (14)..(14)
<223> OTHER INFORMATION: 5-methylcytosine/Beta-D-oxy LNA monomer
<220> FEATURE:
<221> NAME/KEY: modified_base
<222> LOCATION: (17)..(17)
<223> OTHER INFORMATION: 5-methylcytosine/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 18
cuuacgcuga guacuucgat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 5-methylcytosine/Beta-D-oxy LNA monomer
<220> FEATURE:
<221> NAME/KEY: modified_base
<222> LOCATION: (3)..(8)
<223> OTHER INFORMATION: Beta-D-oxy LNA monomer
<220> FEATURE:
<221> NAME/KEY: modified_base
<222> LOCATION: (9)..(9)
<223> OTHER INFORMATION: 5-methylcytosine/Beta-D-oxy LNA monomer
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (11)..(11)
<223> OTHER INFORMATION: 5-methylcytosine/Beta-D-oxy LNA monomer
<220> FEATURE:
<221> NAME/KEY: modified_base
<222> LOCATION: (12)..(13)
<223> OTHER INFORMATION: Beta-D-oxy LNA monomer
<220> FEATURE:
<221> NAME/KEY: modified_base
<222> LOCATION: (14)..(14)
<223> OTHER INFORMATION: 5-methylcytosine/Beta-D-oxy LNA monomer
<220> FEATURE:
<221> NAME/KEY: modified_base
<222> LOCATION: (15)..(21)
<223> OTHER INFORMATION: Beta-D-oxy LNA monomer

<400> SEQUENCE: 19
ucgaagtact cagcgtaagt t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 5-methylcytosine/Beta-D-oxy LNA monomer
<220> FEATURE:
<221> NAME/KEY: modified_base
<222> LOCATION: (4)..(4)
<223> OTHER INFORMATION: Beta-D-oxy LNA monomer
<220> FEATURE:
<221> NAME/KEY: modified_base
<222> LOCATION: (6)..(6)
<223> OTHER INFORMATION: Beta-D-oxy LNA monomer
<220> FEATURE:
<221> NAME/KEY: modified_base
<222> LOCATION: (8)..(8)
<223> OTHER INFORMATION: Beta-D-oxy LNA monomer
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (12)..(12)
<223> OTHER INFORMATION: Beta-D-oxy LNA monomer
<220> FEATURE:
<221> NAME/KEY: modified_base
<222> LOCATION: (14)..(14)
<223> OTHER INFORMATION: 5-methylcytosine/Beta-D-oxy LNA monomer
```

<220> FEATURE:
<221> NAME/KEY: modified_base
<222> LOCATION: (16)..(16)
<223> OTHER INFORMATION: Beta-D-oxy LNA monomer
<220> FEATURE:
<221> NAME/KEY: modified_base
<222> LOCATION: (18)..(18)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 20
ucgaagtact cagcgtaagt t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 5-methylcytosine/Beta-D-oxy LNA monomer
<220> FEATURE:
<221> NAME/KEY: modified_base
<222> LOCATION: (5)..(5)
<223> OTHER INFORMATION: Beta-D-oxy LNA monomer
<220> FEATURE:
<221> NAME/KEY: modified_base
<222> LOCATION: (8)..(8)
<223> OTHER INFORMATION: Beta-D-oxy LNA monomer
<220> FEATURE:
<221> NAME/KEY: modified_base
<222> LOCATION: (11)..(11)
<223> OTHER INFORMATION: 5-methylcytosine/Beta-D-oxy LNA monomer
<220> FEATURE:
<221> NAME/KEY: modified_base
<222> LOCATION: (14)..(14)
<223> OTHER INFORMATION: 5-methylcytosine/Beta-D-oxy LNA monomer
<220> FEATURE:
<221> NAME/KEY: modified_base
<222> LOCATION: (17)..(17)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 21
ucgaagtact cagcgtaagt t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: Beta-D-oxy LNA monomer
<220> FEATURE:
<221> NAME/KEY: modified_base
<222> LOCATION: (6)..(6)

<223> OTHER INFORMATION: Beta-D-oxy LNA monomer
<220> FEATURE:
<221> NAME/KEY: modified_base
<222> LOCATION: (9)..(9)
<223> OTHER INFORMATION: 5-methylcytosine/Beta-D-oxy LNA monomer
<220> FEATURE:
<221> NAME/KEY: modified_base
<222> LOCATION: (12)..(12)
<223> OTHER INFORMATION: Beta-D-oxy LNA monomer
<220> FEATURE:
<221> NAME/KEY: modified_base
<222> LOCATION: (15)..(15)
<223> OTHER INFORMATION: Beta-D-oxy LNA monomer
<220> FEATURE:
<221> NAME/KEY: modified_base
<222> LOCATION: (17)..(17)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 22
ucgaaguacu cagcguaagt t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 5-methylcytosine/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 23
ucgaaguacu cagcguaagt t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 24
ucgaaguacu cagcguaagt t                                              21

<210> SEQ ID NO 25
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 25
ucgaaguacu cagcguaagt t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 26
ucgaaguacu cagcguaagt t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 27
ucgaaguacu cagcguaagt t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (3)..(3)
<223> OTHER INFORMATION: Beta-D-oxy LNA monomer
<220> FEATURE:
<221> NAME/KEY: modified_base
<222> LOCATION: (5)..(5)
<223> OTHER INFORMATION: Beta-D-oxy LNA monomer
<220> FEATURE:
<221> NAME/KEY: modified_base
<222> LOCATION: (9)..(9)
<223> OTHER INFORMATION: Beta-D-oxy LNA monomer
<220> FEATURE:
<221> NAME/KEY: modified_base
<222> LOCATION: (12)..(12)
<223> OTHER INFORMATION: Beta-D-oxy LNA monomer
<220> FEATURE:
<221> NAME/KEY: modified_base
<222> LOCATION: (14)..(14)
<223> OTHER INFORMATION: Beta-D-oxy LNA monomer
<220> FEATURE:
<221> NAME/KEY: modified_base
<222> LOCATION: (17)..(17)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 28
tgagagaaag cacagaaaat t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 29
tgagagaaag cacagaaaat t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer
```

<400> SEQUENCE: 30
tuuucugugc uuucucucat t                                             21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 31
ggaugaggaa ggcaauuuat t                                             21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 32
uaaauugccu uccucaucct t                                             21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 33
cugguacgau uucggugaut t                                             21

<210> SEQ ID NO 34
<211> LENGTH: 21
<212> TYPE: DNA
<213> ORGANISM: Artificial Sequence
<220> FEATURE:

-continued

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 34
aucaccgaaa ucguaccagt t                                            21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 35
acugucaaac ccgguaauut t                                            21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 36
aauuaccggg uuugacagut t                                            21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 37

-continued gacaacuccu auucguagut t                                          21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 38
acuacgaaua ggaguuguct t                                          21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 39
uccagaacaa accaaacggt t                                          21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 40
aaacaugcag aaaaugcugt t                                          21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 5-methylcytosine/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 41
ucgaaguacu cagcguaagt t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 42
ucgaaguact cagcguaagt t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (11)..(11)
<223> OTHER INFORMATION: 5-methylcytosine/Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 43
ucgaaguacu cagcguaagt t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: Beta-D-oxy LNA monomer
```

```
<220> FEATURE:
<221> NAME/KEY: modified_base
<222> LOCATION: (20)..(21)
<223> OTHER INFORMATION: Beta-D-oxy LNA monomer

<400> SEQUENCE: 44
ucgaaguacu cagcguaagt t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 45
ucgaaguaca cagcguaagt t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 46
gcugacccug aaguucauct t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (2)..(2)
<223> OTHER INFORMATION: 5-methylcytosine/Beta-D-oxy LNA monomer
<220> FEATURE:
<221> NAME/KEY: modified_base
<222> LOCATION: (3)..(3)
```

<223> OTHER INFORMATION: Beta-D-oxy LNA monomer
<220> FEATURE:
<221> NAME/KEY: modified_base
<222> LOCATION: (7)..(7)
<223> OTHER INFORMATION: 5-methylcytosine/Beta-D-oxy LNA monomer
<220> FEATURE:
<221> NAME/KEY: modified_base
<222> LOCATION: (10)..(10)
<223> OTHER INFORMATION: Beta-D-oxy LNA monomer
<220> FEATURE:
<221> NAME/KEY: modified_base
<222> LOCATION: (14)..(15)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 47
gctgacccug aagttcauct t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Beta-D-oxy LNA monomer

<400> SEQUENCE: 48
gaugaacuuc agggucagct t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
ugagagaaag cacagaaaat t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
uuuucugugc uuucucucat t                                              21

<210> SEQ ID NO 51
<211> LENGTH: 29
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
ctagcaaact gtcaaacccg gtaattttc                                          29

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
ctaggaaaat taccgggttt gacagtttg                                          29

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
ggaugaggaa ggcaauuuat t                                                  21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
uaaauugccu uccucaucct t                                                  21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
cugguacgau uucggugaut t                                                  21

<210> SEQ ID NO 56
<211> LENGTH: 21
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 56
aucaccgaaa ucguaccagt t    21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 57
acugucaaac ccgguaauut t    21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 58
aauuaccggg uuugacagut t    21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 59
gacaacuccu auucguagut t    21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 60
acuacgaaua ggaguuguct t    21

<210> SEQ ID NO 61
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 61
cuuacgcuga guacuucgat t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: Beta-D-oxy LNA monomer
<220> FEATURE:
<221> NAME/KEY: modified_base
<222> LOCATION: (8)..(8)
<223> OTHER INFORMATION: Beta-D-oxy LNA monomer
<220> FEATURE:
<221> NAME/KEY: modified_base
<222> LOCATION: (12)..(12)
<223> OTHER INFORMATION: Beta-D-oxy LNA monomer
<220> FEATURE:
<221> NAME/KEY: modified_base
<222> LOCATION: (15)..(16)
<223> OTHER INFORMATION: Beta-D-oxy LNA monomer
<220> FEATURE:
<221> NAME/KEY: modified_base
<222> LOCATION: (20)..(21)
<223> OTHER INFORMATION: Beta-D-oxy LNA monomer

<400> SEQUENCE: 62
cttacgctga gtacttcgat t                                              21
```